United States Patent
Shakhmin et al.

(10) Patent No.: US 11,015,216 B2
(45) Date of Patent: *May 25, 2021

(54) SUBSTITUTED IMIDAZO[1,2-A]PYRAZINES AS LUCIFERASE SUBSTRATES

(71) Applicant: PROMEGA CORPORATION, Madison, WI (US)

(72) Inventors: Anton Shakhmin, Grover Beach, CA (US); Thomas Kirkland, Atascadero, CA (US); Joel Walker, San Luis Obispo, CA (US); Thomas Machleidt, Madison, WI (US); Mary Hall, Waunakee, WI (US); Keith V. Wood, Mount Horeb, WI (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/865,497

(22) Filed: May 4, 2020

(65) Prior Publication Data

US 2020/0263229 A1 Aug. 20, 2020

Related U.S. Application Data

(60) Continuation of application No. 16/390,382, filed on Apr. 22, 2019, now Pat. No. 10,669,568, which is a continuation of application No. 15/887,735, filed on Feb. 2, 2018, now Pat. No. 10,308,975, which is a division of application No. 15/431,961, filed on Feb. 14, 2017, now Pat. No. 9,924,073.

(60) Provisional application No. 62/295,363, filed on Feb. 15, 2016.

(51) Int. Cl.
| | | |
|---|---|---|
| C07D 487/04 | (2006.01) | |
| C12Q 1/66 | (2006.01) | |
| C07D 519/00 | (2006.01) | |
| A61K 49/00 | (2006.01) | |
| G01N 33/58 | (2006.01) | |
| H04N 1/60 | (2006.01) | |

(52) U.S. Cl.
CPC ............ *C12Q 1/66* (2013.01); *A61K 49/0013* (2013.01); *C07D 487/04* (2013.01); *C07D 519/00* (2013.01); *G01N 33/581* (2013.01); *H04N 1/6041* (2013.01); *G01N 2333/90241* (2013.01)

(58) Field of Classification Search
CPC .................................................. C07D 487/04
USPC ....................................................... 544/350
See application file for complete search history.

(56) References Cited

U.S. PATENT DOCUMENTS

| | | | |
|---|---|---|---|
| 7,425,436 | B2 | 9/2008 | Darzins et al. |
| 7,537,912 | B2 | 5/2009 | Wood et al. |
| 8,026,363 | B2 | 9/2011 | Satoshi |
| 8,431,525 | B2 | 4/2013 | Hosoya et al. |
| 8,471,015 | B2 | 6/2013 | Inouye |
| 8,546,568 | B2 | 10/2013 | Inouye et al. |
| 8,642,281 | B2 | 2/2014 | Inouye et al. |
| 8,765,921 | B2 | 7/2014 | Inouye et al. |
| 8,772,484 | B2 | 7/2014 | Inouye et al. |
| 8,809,529 | B2 | 8/2014 | Klaubert et al. |
| 8,871,931 | B2 | 10/2014 | Inouye |
| 8,883,432 | B2 | 11/2014 | Inouye et al. |
| 8,975,403 | B2 | 3/2015 | Inouye et al. |
| 9,056,840 | B2 | 6/2015 | Inouye et al. |
| 9,075,058 | B2 | 7/2015 | Inouye et al. |
| 9,151,739 | B2 | 10/2015 | Inouye et al. |
| 2012/0117667 | A1 | 5/2012 | Klaubert et al. |
| 2014/0302539 | A1 | 10/2014 | Inouye et al. |
| 2015/0119575 | A1 | 4/2015 | Inouye et al. |

(Continued)

FOREIGN PATENT DOCUMENTS

| | | |
|---|---|---|
| EP | 1894933 | 3/2008 |
| EP | 1451155 | 7/2008 |

(Continued)

OTHER PUBLICATIONS

"Vogel's Textbook of Practical Organic Chemistry", 5th edition (1989).

(Continued)

*Primary Examiner* — Douglas M Willis
(74) *Attorney, Agent, or Firm* — Casimir Jones, S.C.; Anne M. Reynolds

(57) ABSTRACT

Described are substituted imidazo[1,2-a]pyrazine compounds, which are coelenterazine analogues, kits comprising the compounds, and methods of using the compounds for the detection of luminescence in luciferase-based assays. Also described are methods of making the compounds, such as a method using aminopyrazine acetophosphonates as synthesis intermediates. The substituted imidazo[1,2-a]pyrazine compounds include compounds of formula (I):

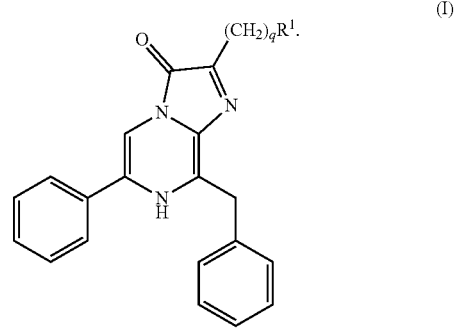

8 Claims, 6 Drawing Sheets

(56) References Cited

U.S. PATENT DOCUMENTS

| | | | |
|---|---|---|---|
| 2015/0212078 | A1 | 7/2015 | Zhou et al. |
| 2015/0266833 | A1 | 9/2015 | Inouye et al. |
| 2015/0344936 | A1 | 12/2015 | Inouye et al. |

FOREIGN PATENT DOCUMENTS

| | | |
|---|---|---|
| JP | 2013-544242 A | 12/2013 |
| JP | 2014-201565 A | 10/2014 |
| WO | WO2003/040100 | 5/2003 |
| WO | WO2012/061529 | 5/2012 |
| WO | WO2012/061530 | 5/2012 |

OTHER PUBLICATIONS

Adamczyk et al., "Synthesis of coelenterazine." Organic Preparations and Procedures International 33, No. 5 (2001): 477-485.
Anton Shakhmin et al: "Three Efficient Methods for Preparation of Coelenterazine Analogues", Chemistry—A European Journal, vol. 22, No. 30, Jun. 15, 2016, pp. 10369-10375.
Boutagy et al., "Olefin Synthesis with Organic Phosphonate Carbanions," Chem. Rev. 1974, 74, 87.
Brown et al., "Synthesis of N-aryl indole-2-carboxylates via an intramolecular palladiumcatalysed annulation of didehydrophenylalanine derivatives," Tetrahedron Letters, 2000, vol. 41, Issue 10, pp. 1623-1626.
Carruthers, Some Modern Methods of Organic Synthesis, 3rd Edition, Cambridge University Press, Cambridge, 1987.
Cevenini et al., "Luciferase Genes as Reporter Reactions: How to Use Them in Molecular Biology?" Adv Biochem Eng Biotechnol., 2016, 154: 3-17.
Clayden et al., "Stereocontrol in Organic Synthesis Using the Diphenylphosphoryl Group," Angew. Chem. Int. Ed. Engl. 1996, 35, 241-70.
Davies et al., "Catalytic C—H functionalization by metal carbenoid and nitrenoid insertion," Nature 2008, 451, 417-424.
Davies et al., "Catalytic Enantioselective C—H Activation by Means of Metal—Carbenoid-Induced C—H Insertion," J. Chem. Rev. 2003, 103, 2861.
Doshi et al., "Luciferin IPA—Based Higher Throughput Human Hepatocyte Screening Assays for CYP3A4 Inhibition and Induction." Journal of biomolecular screening 16, No. 8 (2011): 903-909.
Doyle et al., "Recent Advances in Asymmetric Catalytic Metal Carbene Transformations," Chem. Rev. 1998, 98, 911.
Fan et al., "Novel genetically encoded biosensors using firefly luciferase." ACS chemical biology 3, No. 6 (2008): 346-351.
Guo, "Using the newly developed nanoluciferase as an ultrasensitive bioluminescent probe for ligand-receptor interaction studies." Receptors & Clinical Investigation 1, No. 2 (2014): 1-3.
Hall et al., "Engineered luciferase reporter from a deep sea shrimp utilizing a novel imidazopyrazinone substrate." ACS chemical biology 7, No. 11 (2012): 1848-1857.
Inoue et al., "Squid bioluminescence II. Isolation from Watasenia scintilians and synthesis of 2-(p-hydroxybenzyl)-6-(p-hydroxyphenyl)-3, 7-dihydroimidazo (1, 2-a) pyrazin-3-one." Chemistry Letters 2 (1975): 141-144.
Inouye et al., "C6-Deoxy coelenterazine analogues as an efficient substrate for glow luminescence reaction of nanoKAZ: the mutated catalytic 19kDa component of Oplophorus luciferase." Biochemical and biophysical research communications 437, No. 1 (2013): 23-28.
International Search Report for Application No. PCT/US2017/017761 dated Mar. 23, 2017 (20 pages).
International Union of Pure Applied Chemistry, "Rules for the Nomenclature of Organic Chemistry" Collators: Cross and Klyne, 1976, 45: 13-30.
Kondo et al., "Novel synthetic route of coelenterazines-2-: Synthesis of various dehydrocoelenterazine analogs." Heterocycles-Sendai Institute of Heterocyclic Chemistry 65, No. 4 (2005): 843-856.
Kürti et al., Strategic Applications of Named Reactions in Organic Synthesis, Elsevier, 2005, p. 376-377.
Larock, Comprehensive Organic Transformations, VCH Publishers, Inc., New York, 1989.
Masuho et al., "Monitoring G Protein Activation in Cells with BRET." G Protein-Coupled Receptors in Drug Discovery: Methods and Protocols (2015): 107-113.
Melnick et al., "An efficient rapid system for profiling the cellular activities of molecular libraries." Proceedings of the National Academy of Sciences of the United States of America 103, No. 9 (2006): 3153-3158.
Minami et al., "Vinylphosphonates in Organic Synthesis," J.Synthesis 1992, 333.
Minami et al., "α-Phosphonovinyl Carbanions in Organic Synthesis," Synthesis 2001, 349-57.
Nakamura et al., "Design, synthesis, and evaluation of the transition-state inhibitors of coelenterazine bioluminescence: Probing the chiral environment of active site." Journal of the American Chemical Society 123, No. 7 (2001): 1523-1524.
Padwa et al., "Cascade Processes of Metallo Carbenoids," Chem. Rev. 1996, 96, 223.
Perroy et al., "Real-time monitoring of ubiquitination in living cells by BRET." Nature Methods 1, No. 3 (2004): 203-208.
Remy et al., "A highly sensitive protein-protein interaction assay based on Gaussia luciferase." Nature methods 3, No. 12 (2006): 977-979.
Roda et al., "Bioluminescence in analytical chemistry and in vivo imaging." TrAC Trends in Analytical Chemistry 28, No. 3 (2009): 307-322.
Saito et al., "Recent progress in luminescent proteins development." Current opinion in chemical biology 27 (2015): 46-51.
Shrestha et al., "Strategies for Large-Scale Synthesis of Coelenterazine for in Vivo Applications." Synthesis 46, No. 05 (2014): 646-652.
Smirnova et al. "Development of Neh2-luciferase reporter and its application for high throughput screening and real-time monitoring of Nrf2 activators." Chemistry & biology 18, No. 6 (2011): 752-765.
Smith and March March's Advanced Organic Chemistry, 5th Edition, John Wiley & Sons, Inc., New York, 2001.
Sorrell, Organic Chemistry, University Science Books, Sausalito, 1999.
Stacer et al., "NanoLuc reporter for dual luciferase imaging in living animals." Molecular imaging 12, No. 7 (2013): 1.
Stec, "Wadsworth-Emmons Reaction Revisited," Acc. Chem. Res. 1983, 16, 411.
Wadsworth et al., "Synthetic Applications of Phosphoryl Stabilized Anions," Org. React. 1977, 25, 73.
Wang et al. "The Catalytic Asymmetric Claisen Rearrangement (CAC) in Natural Product Synthesis: Synthetic Studies Toward (-)-Ecklonialactone B," Synlett, 2007, 11, 1683-1686.
Williams et al., "pKa data compiled by R. Williams." (2004).
Woo et al., "Structure-function studies on the active site of the coelenterazine-dependent luciferase from Renilla." Protein Science 17, No. 4 (2008): 725-735.
Wuts and TW Greene, in Greene's book titled Protective Groups in Organic Synthesis (4th ed.), John Wiley & Sons, NY (2006).
Yamazaki et al., "Immobilized α-diazophosphonoacetate as a versatile key precursor for palladium catalyzed indole synthesis on a polymer support," Chemical Communications, 2002, 210-211.
Zhao et al., "Characterization of coelenterazine analogs for measurements of Renilla luciferase activity in live cells and living animals." Molecular imaging 3 (2004): 43-54.
Hart, et al., "Renilla Reniformis Bioluminescence: Luciferase-Catalyzed Production of Nonradiating Excited States From Luciferin Analogues and Elucidation of the Excited State Species Involved in Energy Transfer to Renilla Green Fluorescent Protein," Biochemistry, 1979, 18(11), 2204-2210.
Inoue et al., "Chemical studies of myctophina fish bioluminescence," Chemistry Letters (1987), (2), 417-18.
Kakoi et al., "A New Synthesis of Watasenia Preluciferin by Cyclization of 2-Amino-3-Benzyl-5-(p-Hydroxyphenyl)Pyrazine with p-Hydroxyphenylpyruviacc," Chem. Lett., 1980, 11(3):299-300.
Kakoi, "Synthesis of 2-Amino-3-benzyl-5-(p-hydroxyphenyl)pyrazine" Chem. Pharm. Bull., 2002, 50:301.

(56) References Cited

OTHER PUBLICATIONS

Saito, et al., "Substituent effects on the chemiluminescent properties of coelenterazine analogs," Chemistry Letters, 1998, vol. 1, pp. 95-96.

Shimomura et al., "Semi-synthetic aequorin. An improved tool for the measurement of calcium concentration," Biochemical Journal, 1988, vol. 251, No. 2, pp. 405-410.

Shakhmin et al., "Three Efficient Methods for Preparation of Coelenterazine Analogues," (2016) 22 *Chem. Eur. J.* 10369-10375.

SUBSTITUTED IMIDAZO[1,2-A]PYRAZINES AS LUCIFERASE SUBSTRATES

CROSS-REFERENCE TO RELATED APPLICATIONS

This application is a continuation of U.S. patent application Ser. No. 16/390,382, filed on Apr. 22, 2019, now U.S. Pat. No. 10,669,568, which is a continuation of U.S. patent application Ser. No. 15/887,735, filed on Feb. 2, 2018, now U.S. Pat. No. 10,308,975, which is a divisional of U.S. patent application Ser. No. 15/431,961, filed on Feb. 14, 2017, now U.S. Pat. No. 9,924,073, which claims priority to U.S. Provisional Patent Application No. 62/295,363, filed on Feb. 15, 2016, the entire contents of each of which are incorporated herein by reference.

TECHNICAL FIELD

The present disclosure relates to coelenterazine analogues, methods for making coelenterazine analogues, and methods of using coelenterazine analogues in luciferase-based assays.

BACKGROUND

Bioluminescent assays are used extensively in the investigation of cellular physiology, especially processes associated with gene expression. In particular, luciferase reporter enzymes are quite valuable tools in this field, and, to date, there has been intense protein engineering to obtain small and environmentally insensitive luciferases that may be useful in bioluminescent assays. There exist a number of efficient luciferase reporters enabling whole-cell biosensor measurements, drug discovery through high-throughput screening, and in vivo imaging, which also permits the study of protein-protein interactions in living cells, apoptosis, and cell viability. Luciferases that use coelenterazine and coelenterazine analogues as substrates are among the most widely used systems due to their brightness and acceptance in whole cell applications.

SUMMARY OF THE INVENTION

Many known coelenterazine analogues have deficiencies, which limit their effectiveness as luciferase substrates and usefulness in luciferase-based luminescence assays. These deficiencies include cell toxicity, light sensitivity, thermodynamic instability, low aqueous solubility, and low cell permeability. Accordingly, there exists a need for coelenterazine analogues with improved properties and methods for synthesizing the analogues.

In one aspect, disclosed are compounds of formula (I),

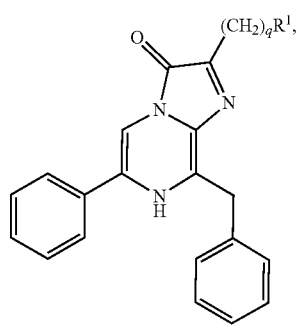

or tautomers, or pharmaceutically acceptable salts thereof, wherein $R^1$ is alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, or phosphonate; and q is 0-2; wherein said alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, and phosphonate, at each occurrence, are independently substituted or unsubstituted.

Also disclosed are methods of making the compounds, kits comprising the compounds, and methods of using the compounds as luciferase substrates in luciferase-based luminescence assays.

DETAILED DESCRIPTION

Figure 1:
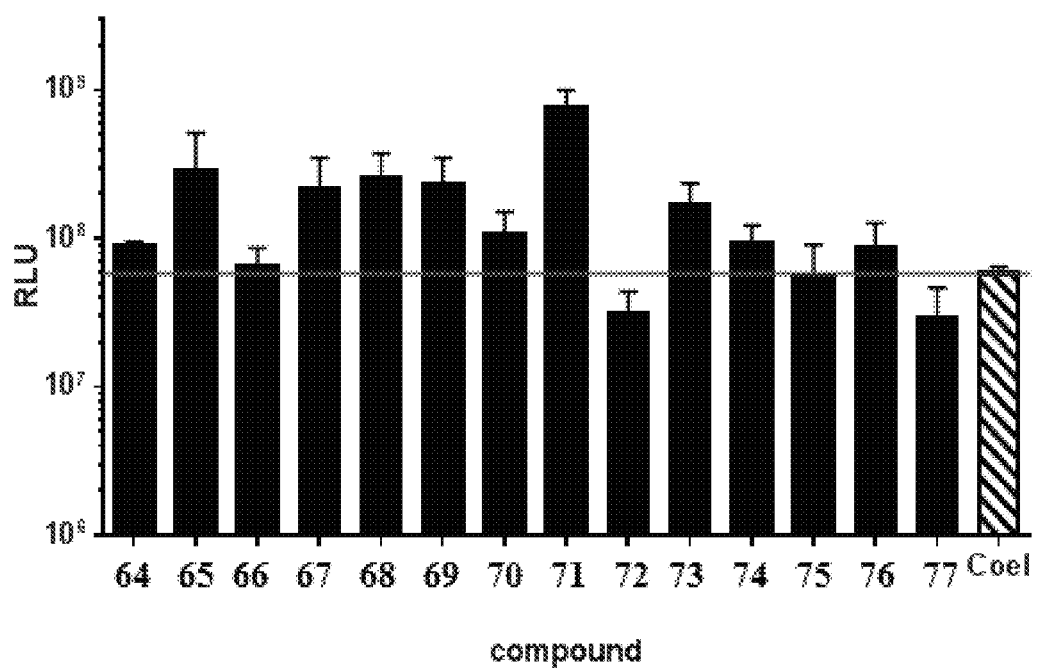
FIG. 1 is a graph depicting cellular bioluminescent activity of exemplary compounds in HEK293 cells in comparison to coelenterazine.

Disclosed herein are coelenterazine analogues. The coelenterazine analogues can be compounds of formula (I) and useful substrates of proteins that utilize coelenterazine to produce luminescence, including, but not limited to, luciferases and photoproteins found in various marine organisms such as cnidarians (e.g., *Renilla* luciferase), jellyfish (e.g., aequorin from the *Aequorea* jellyfish) and decapods luciferases (e.g., luciferase complex of *Oplophorus gracilirostris*). In comparison to coelenterazine, compounds of formula (I) may have at least one of improved water solubility, improved stability, improved cell permeability, increased biocompatibility with cells, reduced autoluminescence, and reduced toxicity.

Also disclosed herein are methods of making coelenterazine analogues [compounds of formula (I)]. Disclosed are three robust and versatile approaches towards the preparation of coelenterazine analogues. The methods allow for the preparation of analogues that could not have been prepared using existing synthetic methods. The described methodology enables access to a variety of substituents at the $R^1$ position and can be performed under mild conditions utilizing a wide variety of readily available starting materials. The disclosed synthetic methodology unexpectedly provides a variety of new applications and advancements in bioluminescence technology based on coelenterazine analogues.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 10 carbon atoms with at least one carbon-carbon double bond. The alkenyl group may be substituted or unsubstituted. For example, the alkenyl group may be substituted with an aryl group, such as a phenyl.

The term "alkynyl" as used herein, means a hydrocarbon chain containing from 2 to 10 carbon atoms with at least one carbon-carbon triple bond. The alkynyl group may be substituted or unsubstituted. For example, the alkynyl group may be substituted with an aryl group, such as a phenyl.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

Disclosed are compounds of formula (I):

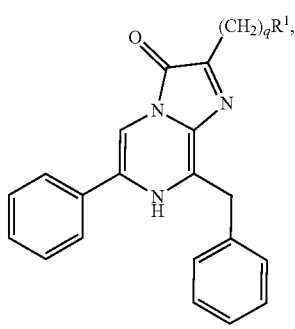

(I)

or tautomers, or pharmaceutically acceptable salts thereof, wherein $R^1$ is alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, or phosphonate; and q is 0-2; wherein said alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, and phosphonate, at each occurrence, are independently substituted or unsubstituted.

In certain embodiments, $R^1$ is alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, or phosphonate; and q is 0-2; wherein said alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, and phosphonate, at each occurrence, are independently substituted or unsubstituted with 1, 2, 3, 4, 5, 6, or 7 functional groups independently selected from the group consisting halogen =O, =S, cyano, carbamate, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, heterocycloalkyl, cycloalkylalkyl, heteroarylalkyl, arylalkyl, hydroxy, hydroxyalkyl, alkoxy, allyloxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyloxy, t-butyldimethylsilyloxy, alkylsulfanyl, sulfanyl, thiotriazolyl, and acyl.

In certain embodiments, $R^1$ is alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, or phosphonate; and q is 0-2; wherein said alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, and phosphonate, at each occurrence, are independently substituted or unsubstituted;
provided that if q is 0, then
$R^1$ is not $C_1$-$C_5$ alkyl or

wherein $R^a$ is $NH_2$, halogen, OH, $NHC(O)C_1$-$C_7$-alkyl, or $CO_2C_1$-$C_7$-alkyl;
provided that if q is 1, then
$R^1$ is not $C_1$-$C_4$ alkyl,

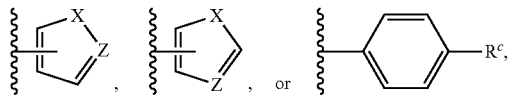

wherein $R^c$ is H, OH, $OC(O)C_1$-$C_7$-alkyl, $OCH_2OC(O)C_1$-$C_7$-alkyl, X is S, O, NH, $NCH_3$, or $NCH_2CH_3$, and Z is CH or N; and
provided that if q is 2, then
$R^1$ is not $C_1$-$C_3$ alkyl; and wherein the compound of formula (I) is not 8-benzyl-2-((1-methyl-1H-imidazol-2-yl)methyl)-6-phenylimidazo[1,2-a]pyrazin-3(7H)-one.

In certain embodiments, $R^1$ is alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, or phosphonate; and q is 0-2; wherein said alkyl, alkenyl, alkynyl, aryl, bicyclic aryl, tricyclic aryl, heteroaryl, bicyclic heteroaryl, tricyclic heteroaryl, heterocycle, cycloalkyl, heteroarylcarbonyl, and phosphonate, at each occurrence, are independently substituted or unsubstituted with 1, 2, 3, 4, 5, 6, or 7 functional groups independently selected from the group consisting of halogen, =O, =S, cyano, carbamate, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, heterocycloalkyl, cycloalkylalkyl, heteroarylalkyl, arylalkyl, hydroxy, hydroxyalkyl, alkoxy, allyloxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyloxy, t-butyldimethylsilyloxy, alkylsulfanyl, sulfanyl, thiotriazolyl, and acyl;
provided that if q is 0, then
$R^1$ is not $C_1$-$C_5$ alkyl or

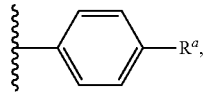

wherein $R^a$ is $NH_2$, halogen, OH, $NHC(O)C_1$-$C_7$-alkyl, or $CO_2C_1$-$C_7$-alkyl;
provided that if q is 1, then
$R^1$ is not $C_1$-$C_4$ alkyl,

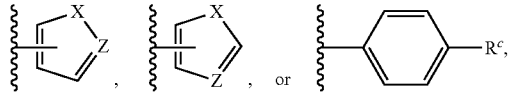

wherein $R^c$ is H, OH, OC(O)$C_1$-$C_7$-alkyl, OCH$_2$OC(O)$C_1$-$C_7$-alkyl, X is S, O, NH, NCH$_3$, or NCH$_2$CH$_3$, and Z is CH or N; and provided that if q is 2, then $R^1$ is not $C_1$-$C_3$ alkyl; and wherein the compound of formula (I) is not 8-benzyl-2-((1-methyl-1H-imidazol-2-yl)methyl)-6-phenylimidazo[1,2-a]pyrazin-3(7H)-one.

In certain embodiments, $R^1$ is phenyl, pyridinyl, benzodioxolyl, benzotriazolyl, thiazolyl, thiadiazolyl, thienopyrrolyl, pyrimidinyl, pyrazinyl, thienothienyl, thienyl, diethylphosphonate, isoxazolyl, imidazothiazolyl, 1,3-dimethylpyrimidine-2,4(1H,3H)-dionyl, furanyl, pyrazolyl, benzothienyl, $C_{10}$-$C_{12}$ alkyl, benzothiazolyl, cinnamyl, dibenzofuranyl, chromenyl or naphthalenyl; and q is 0-2; wherein said phenyl, pyridinyl, benzodioxolyl, benzotriazolyl, thiazolyl, thiadiazolyl, thienopyrrolyl, pyrimidinyl, pyrazinyl, thienothienyl, thienyl, diethylphosphonate, isoxazolyl, imidazothiazolyl, 1,3-dimethylpyrimidine-2,4(1H,3H)-dionyl, furanyl, pyrazolyl, benzothienyl, $C_{10}$-$C_{12}$ alkyl, benzothiazolyl, cinnamyl, dibenzofuranyl, chromenyl and naphthalenyl, at each occurrence, are independently substituted or unsubstituted;

provided that if q is 0, then $R^1$ is not $C_1$-$C_5$ alkyl or

wherein $R^a$ is NH$_2$, halogen, OH, NHC(O)$C_1$-$C_7$-alkyl, or CO$_2$$C_1$-$C_7$-alkyl;

provided that if q is 1, then $R^1$ is not $C_1$-$C_4$ alkyl,

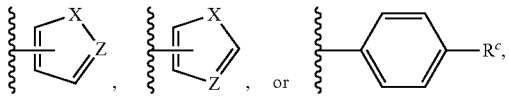

wherein $R^c$ is H, OH, OC(O)$C_1$-$C_7$-alkyl, OCH$_2$OC(O)$C_1$-$C_7$-alkyl, X is S, O, NH, NCH$_3$ or NCH$_2$CH$_3$, and Z is CH or N; and provided that if q is 2, then $R^1$ is not $C_1$-$C_3$ alkyl; and wherein the compound of formula (I) is not 8-benzyl-2-((1-methyl-1H-imidazol-2-yl)methyl)-6-phenylimidazo[1,2-a]pyrazin-3(7H)-one.

In certain embodiments, $R^1$ is phenyl, pyridinyl, benzodioxolyl, benzotriazolyl, thiazolyl, thiadiazolyl, thienopyrrolyl, pyrimidinyl, pyrazinyl, thienothienyl, thienyl, diethylphosphonate, isoxazolyl, imidazothiazolyl, 1,3-dimethylpyrimidine-2,4(1H,3H)-dionyl, furanyl, pyrazolyl, benzothienyl, $C_{10}$-$C_{12}$ alkyl, benzothiazolyl, cinnamyl, dibenzofuranyl, chromenyl or naphthalenyl; and q is 0-2; wherein said phenyl, pyridinyl, benzodioxolyl, benzotriazolyl, thiazolyl, thiadiazolyl, thienopyrrolyl, pyrimidinyl, pyrazinyl, thienothienyl, thienyl, diethylphosphonate, isoxazolyl, imidazothiazolyl, 1,3-dimethylpyrimidine-2,4(1H,3H)-dionyl, furanyl, pyrazolyl, benzothienyl, $C_{10}$-$C_{12}$ alkyl, benzothiazolyl, cinnamyl, dibenzofuranyl, chromenyl and naphthalenyl, at each occurrence, are independently substituted or unsubstituted with 1, 2, 3, 4, 5, 6, or 7 functional groups independently selected from the group consisting of halogen, =O, =S, cyano, carbamate, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, heterocycloalkyl, cycloalkylalkyl, heteroarylalkyl, arylalkyl, hydroxy, hydroxyalkyl, alkoxy, allyloxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyloxy, t-butyldimethylsilyloxy, alkylsulfanyl, sulfanyl, thiotriazolyl, and acyl;

provided that if q is 0, then $R^1$ is not $C_1$-$C_5$ alkyl or

wherein $R^a$ is NH$_2$, halogen, OH, NHC(O)$C_1$-$C_7$-alkyl, or CO$_2$$C_1$-$C_7$-alkyl;

provided that if q is 1, then $R^1$ is not $C_1$-$C_4$ alkyl,

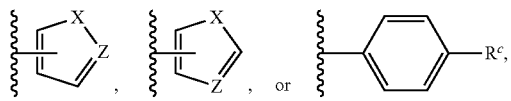

wherein $R^c$ is H, OH, OC(O)$C_1$-$C_7$-alkyl, OCH$_2$OC(O)$C_1$-$C_7$-alkyl, X is S, O, NH, NCH$_3$, or NCH$_2$CH$_3$, and Z is CH or N; and provided that if q is 2, then $R^1$ is not $C_1$-$C_3$ alkyl; and wherein the compound of formula (I) is not 8-benzyl-2-((1-methyl-1H-imidazol-2-yl)methyl)-6-phenylimidazo[1,2-a]pyrazin-3(7H)-one.

Representative compounds of formula (I) include, but are not limited to:

8-benzyl-2-(4-fluorobenzyl)-6-phenylimidazo[1,2-a]pyrazin-3(7H)-one;

8-benzyl-2-(2,4-difluorobenzyl)-6-phenylimidazo[1,2-a]pyrazin-3(7H)-one;

8-benzyl-2-(3-methoxybenzyl)-6-phenylimidazo[1,2-a]pyrazin-3(7H)-one;

8-benzyl-2-(4-fluoro-3-methoxybenzyl)-6-phenylimidazo[1,2-a]pyrazin-3(7H)-one;

8-benzyl-2-(3-hydroxybenzyl)-6-phenylimidazo[1,2-a]pyrazin-3(7H)-one;

8-benzyl-2-(4-fluoro-3-hydroxybenzyl)-6-phenylimidazo[1,2-a]pyrazin-3(7H)-one;

8-benzyl-2-(3-fluoro-4-methoxybenzyl)-6-phenylimidazo[1,2-a]pyrazin-3(7H)-one;

8-benzyl-2-(4-fluoro-2-methoxybenzyl)-6-phenylimidazo[1,2-a]pyrazin-3(7H)-one;

8-benzyl-2-(4-methoxybenzyl)-6-phenylimidazo[1,2-a]pyrazin-3(7H)-one;

tert-butyl (3-((8-benzyl-3-oxo-6-phenyl-3,7-dihydroimidazo[1,2-a]pyrazin-2-yl)methyl)phenyl)carbamate;

8-benzyl-2-((5-methoxythiophen-2-yl)methyl)-6-phenylimidazo[1,2-a]pyrazin-3(7H)-one;

2-(3-aminobenzyl)-8-benzyl-6-phenylimidazo[1,2-a]pyrazin-3(7H)-one;

8-benzyl-2-(4-(tert-butyl)benzyl)-6-phenylimidazo[1,2-a]pyrazin-3(7H)-one;

8-benzyl-2-(naphthalen-2-ylmethyl)-6-phenylimidazo[1,2-a]pyrazin-3(7H)-one 2-([1,1'-biphenyl]-4-ylmethyl)-8-benzyl-6-phenylimidazo[1,2-a]pyrazin-3(7H)-one;
2-((2H-chromen-3-yl)methyl)-8-benzyl-6-phenylimidazo[1,2-a]pyrazin-3(7H)-one;
8-benzyl-2-((1,3-diphenyl-1H-pyrazol-4-yl)methyl)-6-phenylimidazo[1,2-a]pyrazin-3(7H)-one;
8-benzyl-2-(dibenzo[b,d]furan-4-ylmethyl)-6-phenylimidazo[1,2-a]pyrazin-3 (7H)-one;
8-benzyl-2-cinnamyl-6-phenylimidazo[1,2-a]pyrazin-3 (7H)-one;
2-((3-acetylbenzo[d]thiazol-2(3H)-ylidene)methyl)-8-benzyl-6-phenylimidazo[1,2-a]pyrazin-3(7H)-one;
tert-butyl (4-((8-benzyl-3-oxo-6-phenyl-3,7-dihydroimidazo[1,2-a]pyrazin-2-yl)methyl)phenyl)carbamate;
2-(4-aminobenzyl)-8-benzyl-6-phenylimidazo[1,2-a]pyrazin-3(7H)-one;
2-(4-(allyloxy)-3-methoxybenzyl)-8-benzyl-6-phenylimidazo[1,2-a]pyrazin-3(7H)-one;
8-benzyl-2-(4-hydroxy-3-methoxybenzyl)-6-phenylimidazo[1,2-a]pyrazin-3(7H)-one;
8-benzyl-2-((5-((4-methyl-4H-1,2,4-triazol-3-yl)thio)furan-2-yl)methyl)-6-phenylimidazo[1,2-a]pyrazin-3 (7H)-one;
8-benzyl-6-phenyl-2-((5-(pyridin-2-yl)thiophen-2-yl)methyl)imidazo[1,2-a]pyrazin-3(7H)-one
2-(benzo[b]thiophen-3-ylmethyl)-8-benzyl-6-phenylimidazo[1,2-a]pyrazin-3(7H)-one;
8-benzyl-2-dodecyl-6-phenylimidazo[1,2-a]pyrazin-3(7H)-one;
2-(benzo[b]thiophen-2-ylmethyl)-8-benzyl-6-phenylimidazo[1,2-a]pyrazin-3(7H)-one;
8-benzyl-6-phenyl-2-(pyridin-4-ylmethyl)imidazo[1,2-a]pyrazin-3(7H)-one;
8-benzyl-2-((5-cyclohexylthiophen-2-yl)methyl)-6-phenylimidazo[1,2-a]pyrazin-3(7H)-one;
2-([2,2'-bithiophen]-5-ylmethyl)-8-benzyl-6-phenylimidazo[1,2-a]pyrazin-3(7H)-one;
8-benzyl-2-((5-isobutylthiophen-2-yl)methyl)-6-phenylimidazo[1,2-a]pyrazin-3(7H)-one;
8-benzyl-2-((5-(1-methyl-5-(trifluoromethyl)-1H-pyrazol-3-yl)thiophen-2-yl)methyl)-6-phenylimidazo[1,2-a]pyrazin-3(7H)-one;
8-benzyl-6-phenyl-2-((5-(trifluoromethyl)furan-2-yl)methyl)imidazo[1,2-a]pyrazin-3(7H)-one;
4-((8-benzyl-3-oxo-6-phenyl-3,7-dihydroimidazo[1,2-a]pyrazin-2-yl)methyl)benzoic acid;
8-benzyl-2-((5-(methoxymethyl)furan-2-yl)methyl)-6-phenylimidazo[1,2-a]pyrazin-3(7H)-one;
8-benzyl-2-((perfluorophenyl)methyl)-6-phenylimidazo[1,2-a]pyrazin-3 (7H)-one;
8-benzyl-2-((1-methyl-3-(thiophen-2-yl)-1H-pyrazol-5-yl)methyl)-6-phenylimidazo[1,2-a]pyrazin-3 (7H)-one;
8-benzyl-2-(3,5-bis(trifluoromethyl)benzyl)-6-phenylimidazo[1,2-a]pyrazin-3(7H)-one;
8-benzyl-2-((5-chloro-1-methyl-3-(trifluoromethyl)-1H-pyrazol-4-yl)methyl)-6-phenylimidazo[1,2-a]pyrazin-3 (7H)-one;
8-benzyl-2-((5-methylfuran-2-yl)methyl)-6-phenylimidazo[1,2-a]pyrazin-3(7H)-one;
3-((8-benzyl-3-oxo-6-phenyl-3,7-dihydroimidazo[1,2-a]pyrazin-2-yl)methyl)benzoic acid;
8-benzyl-2-((5-(morpholinomethyl)furan-2-yl)methyl)-6-phenylimidazo[1,2-a]pyrazin-3(7H)-one;
2-(3-(aminomethyl)benzyl)-8-benzyl-6-phenylimidazo[1,2-a]pyrazin-3 (7H)-one;
5-((8-benzyl-3-oxo-6-phenyl-3,7-dihydroimidazo[1,2-a]pyrazin-2-yl)methyl)-1,3-dimethylpyrimidine-2,4(1H,3H)-dione;
8-benzyl-2-(imidazo[2,1-b]thiazol-6-ylmethyl)-6-phenylimidazo[1,2-a]pyrazin-3(7H)-one;
N-(3-((8-benzyl-3-oxo-6-phenyl-3,7-dihydroimidazo[1,2-a]pyrazin-2-yl)methyl)phenyl)methanesulfonamide;
8-benzyl-2-((3,5-dimethylisoxazol-4-yl)methyl)-6-phenylimidazo[1,2-a]pyrazin-3(7H)-one;
8-benzyl-6-phenyl-2-(pyridin-3-ylmethyl)imidazo[1,2-a]pyrazin-3(7H)-one; diethyl (8-benzyl-3-oxo-6-phenyl-3,7-dihydroimidazo[1,2-a]pyrazin-2-yl)phosphonate;
8-benzyl-2-(4-methoxy-3-(methoxymethyl)benzyl)-6-phenylimidazo[1,2-a]pyrazin-3(7H)-one;
8-benzyl-2-(3-(dimethylamino)benzyl)-6-phenylimidazo[1,2-a]pyrazin-3(7H)-one;
8-benzyl-2-((5-(methoxymethyl)thiophen-2-yl)methyl)-6-phenylimidazo[1,2-a]pyrazin-3(7H)-one;
8-benzyl-2-(3-(methoxymethyl)benzyl)-6-phenylimidazo[1,2-a]pyrazin-3(7H)-one;
8-benzyl-2-(3-(hydroxymethyl)benzyl)-6-phenylimidazo[1,2-a]pyrazin-3(7H)-one;
8-benzyl-2-((2-methoxypyrimidin-5-yl)methyl)-6-phenylimidazo[1,2-a]pyrazin-3(7H)-one;
8-benzyl-2-((3,4-dimethylthieno[2,3-b]thiophen-2-yl)methyl)-6-phenylimidazo[1,2-a]pyrazin-3(7H)-one;
8-benzyl-6-phenyl-2-(pyrazin-2-ylmethyl)imidazo[1,2-a]pyrazin-3(7H)-one;
8-benzyl-6-phenyl-2-((2-(propylthio)pyrimidin-5-yl)methyl)imidazo[1,2-a]pyrazin-3(7H)-one;
8-benzyl-2-((4-methyl-4H-thieno[3,2-b]pyrrol-5-yl)methyl)-6-phenylimidazo[1,2-a]pyrazin-3(7H)-one;
2-((1,2,3-thiadiazol-5-yl)methyl)-8-benzyl-6-phenylimidazo[1,2-a]pyrazin-3(7H)-one;
8-benzyl-2-((1-methyl-1H-benzo[d][1,2,3]triazol-5-yl)methyl)-6-phenylimidazo[1,2-a]pyrazin-3(7H)-one;
8-benzyl-2-(3,4-dimethoxybenzyl)-6-phenylimidazo[1,2-a]pyrazin-3 (7H)-one;
8-benzyl-2-(3-(methylthio)benzyl)-6-phenylimidazo[1,2-a]pyrazin-3(7H)-one;
2-(benzo[d][1,3]dioxol-5-ylmethyl)-8-benzyl-6-phenylimidazo[1,2-a]pyrazin-3 (7H)-one;
8-benzyl-2-(3-((dimethylamino)methyl)benzyl)-6-phenylimidazo[1,2-a]pyrazin-3(7H)-one;
8-benzyl-2-(3-ethoxybenzyl)-6-phenylimidazo[1,2-a]pyrazin-3(7H)-one;
8-benzyl-2-((6-methylpyridin-3-yl)methyl)-6-phenylimidazo[1,2-a]pyrazin-3 (7H)-one;
8-benzyl-2-((6-(dimethylamino)pyridin-3-yl)methyl)-6-phenylimidazo[1,2-a]pyrazin-3(7H)-one;
8-benzyl-2-((5-methoxypyridin-3-yl)methyl)-6-phenylimidazo[1,2-a]pyrazin-3(7H)-one;
8-benzyl-2-((6-methoxypyridin-3-yl)methyl)-6-phenylimidazo[1,2-a]pyrazin-3(7H)-one;
8-benzyl-2-((6-fluoropyridin-3-yl)methyl)-6-phenylimidazo[1,2-a]pyrazin-3(7H)-one;
8-benzyl-6-phenyl-2-(2,4,6-trifluorobenzyl)imidazo[1,2-a]pyrazin-3 (7H)-one;
8-benzyl-2-((2,6-dimethoxypyridin-3-yl)methyl)-6-phenylimidazo[1,2-a]pyrazin-3(7H)-one;
8-benzyl-2-((6-chloro-4-methoxypyridin-3-yl)methyl)-6-phenylimidazo[1,2-a]pyrazin-3(7H)-one;
8-benzyl-2-((6-fluoro-2-methoxypyridin-3-yl)methyl)-6-phenylimidazo[1,2-a]pyrazin-3(7H)-one;
8-benzyl-2-((2-fluoro-6-methoxypyridin-3-yl)methyl)-6-phenylimidazo[1,2-a]pyrazin-3(7H)-one;
8-benzyl-2-((5-fluoropyridin-3-yl)methyl)-6-phenylimidazo[1,2-a]pyrazin-3(7H)-one;
8-benzyl-2-((2,6-difluoropyridin-3-yl)methyl)-6-phenylimidazo[1,2-a]pyrazin-3(7H)-one;

8-benzyl-2-((6-bromopyridin-3-yl)methyl)-6-phenylimidazo[1,2-a]pyrazin-3(7H)-one;
8-benzyl-2-((6-chloropyridin-3-yl)methyl)-6-phenylimidazo[1,2-a]pyrazin-3(7H)-one;
8-benzyl-2-((2-fluoropyridin-3-yl)methyl)-6-phenylimidazo[1,2-a]pyrazin-3(7H)-one;
8-benzyl-2-((2,6-dichloropyridin-3-yl)methyl)-6-phenylimidazo[1,2-a]pyrazin-3(7H)-one;
8-benzyl-6-phenyl-2-styryl-1,7-dihydroimidazo[1,2-a]pyrazin-3(2H)-one;
8-benzyl-2-(3-(2-methoxyethoxy)benzyl)-6-phenylimidazo[1,2-a]pyrazin-3(7H)-one;
3-((8-benzyl-3-oxo-6-phenyl-3,7-dihydroimidazo[1,2-a]pyrazin-2-yl)methyl)benzonitrile;
and pharmaceutically acceptable salts thereof.

Compound names are assigned by using Struct=Name naming algorithm as part of CHEMDRAW® ULTRA v. 12.0.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Fumiss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms, as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Properties of the Compounds of Formula (I)

The compounds of formula (I) may be substrates of luciferases to produce luminescence. The compounds may have improved water solubility, improved stability, improved cell permeability, increased biocompatibility with cells, reduced autoluminescence, and reduced toxicity.

"Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the coelenterazine substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., coelenterazine analogue, buffer, etc., into a reaction chamber (e.g., a well of a multiwell plate such as a 96-well plate) containing the luminescent protein. In still other embodiments, the luciferase and/or coelenterazine analogues (e.g., compounds of formula (I)) are introduced into a host and measurements of luminescence are made on the host or a portion thereof, which can include a whole organism or cells, tissues, explants, or extracts thereof. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

Compounds of formula (I) can have an RLU of greater than or equal to 1, greater than or equal to 2, greater than or equal to 3, greater than or equal to 4, greater than or equal to 5, greater than or equal to 10, greater than or equal to 20, greater than or equal to 30, greater than or equal to 40, greater than or equal to 50, or greater than or equal to 100, relative to coelenterazine or a known coelenterazine analogue.

"Biocompatibility" refers to the tolerance of a cell (e.g., prokaryotic or eukaryotic) to a coelenterazine analogue (e.g., compounds of formula (I)). Biocompatibility of a coelenterazine analogue is related to the stress it causes on the host cell.

Enhanced biocompatibility of the coelenterazine analogues (e.g., compounds of formula (I)), may be determined by measuring cell viability and/or growth rate of cells. For example, enhanced biocompatibility of the coelenterazine analogues may be determined by measuring cell viability in the absence of luciferase expression of cells exposed to the coelenterazine analogues compared to native or known coelenterazines to determine how compatible and/or toxic the coelenterazine analogues are to the cells.

In particular, enhanced biocompatibility may be determined using cell viability analysis (e.g., using the CELL-TITER-GLO® Luminescent Cell Viability assay), an apoptosis assay (e.g., using the CASPASE-GLO® technology), or another method known in the art. The effect of the compounds of formula (I) on cell viability or apoptosis may be compared to the effect of native or known coelenterazine analogues on cell viability or apoptosis.

Enhanced biocompatibility may also be determined by measuring the effect of the coelenterazine analogues (e.g., compounds of formula (I)) on cell growth or gene expression. For example, enhanced biocompatibility of the compounds of formula (I) may be determined by measuring the cell number after a period of time or by determining the expression of stress response genes in a sample of cells that are exposed to compounds of formula (I) compared to cells exposed to a native or known coelenterazine or no coelenterazine. The effect of the compounds of formula (I) on cell growth or gene expression may be compared to a native or known coelenterazine.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. Synthesis of Compounds of Formula (I)

Current methods that produce coelenterazine analogues employ harsh reaction conditions. The limitations of these synthetic protocols have slowed the investigation of new analogues. In addition, incompatibility of the conditions of these methods with a variety of functional groups and the inability to synthesize ketoaldehyde/ketoacid precursors have led to limited structural alterations at the C-2 position of coelenterazine.

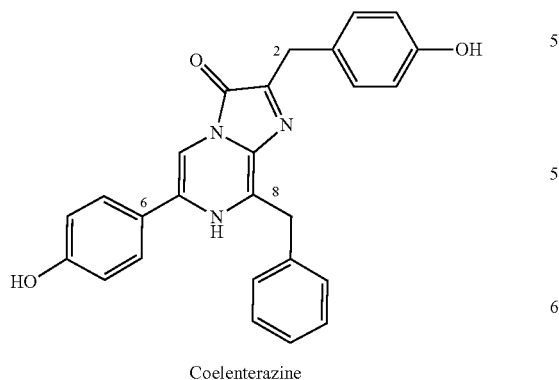

Coelenterazine

Herein, three robust and versatile methods that accomplish the preparation of compounds of formula (I) are described. These methods are useful in preparing analogues that could not be made using existing synthetic methods. The described methodologies enable access to a variety of substituents at the C-2 position and can be performed under relatively mild conditions, utilizing a wide variety of readily available aldehydes as starting materials.

Compounds of formula (I) may be prepared by synthetic processes or by metabolic processes. Preparation of the compounds by metabolic processes includes those occurring in the human or animal body (in vivo) or processes occurring in vitro.

Compounds of formula (I), wherein the groups $R^1$, and q have the meanings as set forth in the Summary of the Invention section unless otherwise noted, can be synthesized as shown in Schemes 1-3.

Abbreviations which have been used in the descriptions of the Schemes that follow are: $Ac_2O$ for acetic anhydride; CDI for carbonyldiimidazole; MeOH for methanol; TMG for 1,1,3,3-tetramethylguanidine; and TFA for trifluoroacetic acid.

Scheme 1. Synthesis of intermediates A-C

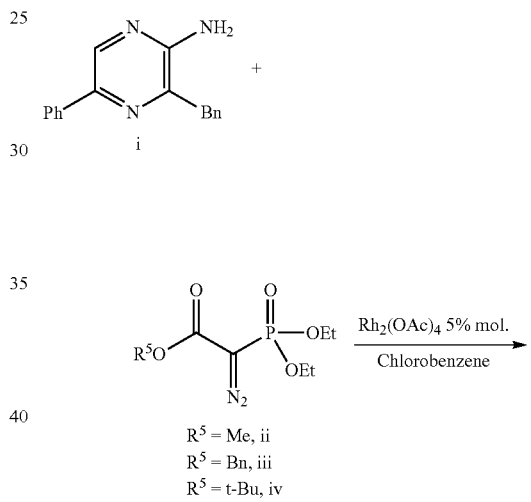

$R^5$ = Me, ii
$R^5$ = Bn, iii
$R^5$ = t-Bu, iv

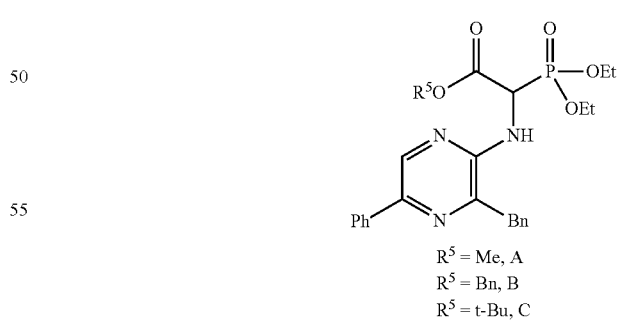

$R^5$ = Me, A
$R^5$ = Bn, B
$R^5$ = t-Bu, C

As shown in Scheme 1, intermediates A-C can be prepared from aminopyrazine i. Treatment of i with diazocarbonyls ii-iv, in the presence of $Rh_2(Oac)_4$, can result in formation of aminopyrazine acetophosphonates A-C. Intermediates A-C may be stable at room temperature and provide starting materials for varied analogues.

Scheme 2. Synthesis of the compound of formula (I)

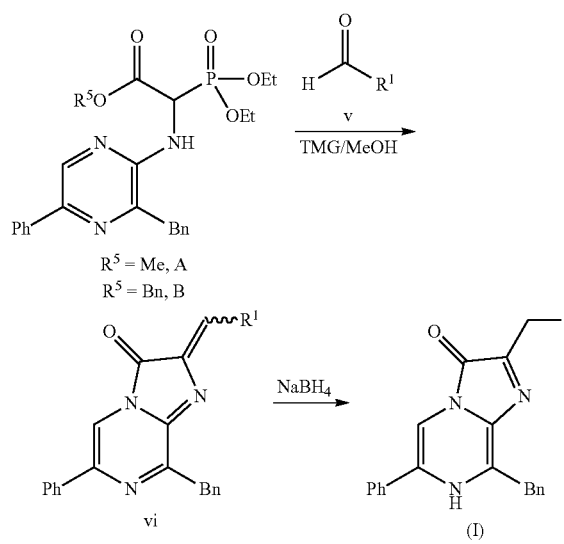

Scheme 2 illustrates the conversion of intermediates A and B to the compound of formula (I), wherein n is 1. Intermediates A and B can be treated with 1,1,3,3-tetramethylguanidine and undergo Horner-Wadsworth-Emmons olefination with aldehyde v, wherein $R^1$ is as defined in the Summary of Invention, to yield intermediate vi. Intermediate vi can be reduced to give the compound of formula (I).

TFA and subsequent cyclization promoted by the addition of carbonyldiimidazole. Alternatively, intermediate vii can be treated with TFA, resulting in hydrolysis of the t-butyl ester and formation of intermediate ix. Addition of acetic anhydride followed by sodium borohydride can then provide the compound of formula (I).

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of

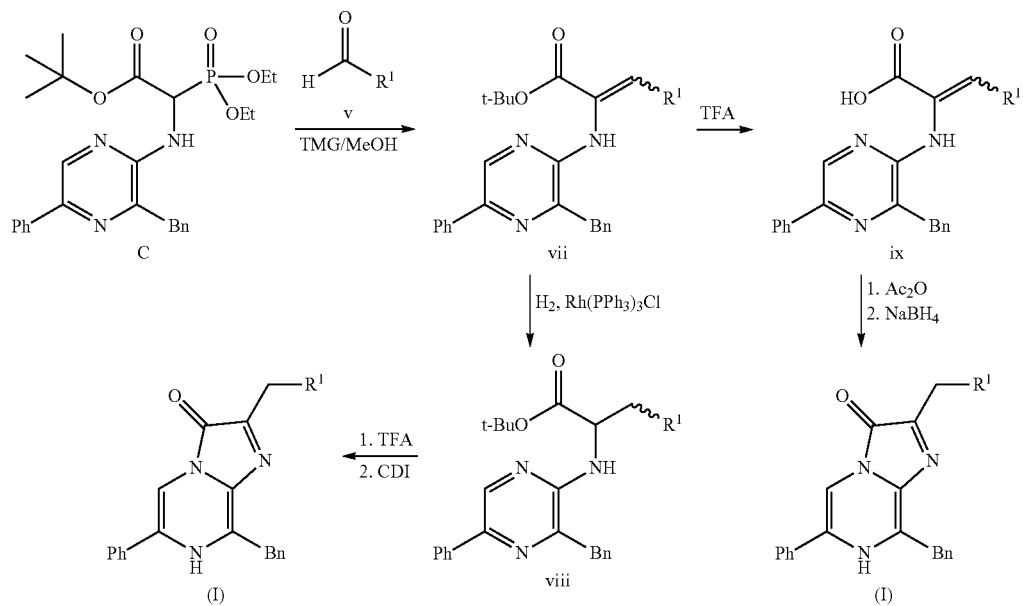

Scheme 3. Synthesis of the compound of formula (I)

Scheme 3 illustrates the preparation of the compound of formula (I) by two routes from intermediate C. Intermediate C can be treated with 1,1,3,3-tetramethylguanidine and undergo Horner-Wadsworth-Emmons olefination with aldehyde v, wherein $R^1$ is as defined in the Summary of Invention, to give intermediate vii. Intermediate vii can be hydrogenated to provide intermediate viii, which can then be converted to the compound of formula (I) by treatment with the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4th ed.), John Wiley & Sons, NY (2006), which is incorporated herein by reference in its entirety.

Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. Methods of Use and Kits

The compounds and proteins of the disclosure may be used in any way that luciferase substrates, e.g., coelenterazine analogues, have been used. For example, they may be used in a bioluminogenic method which employs an analogue of coelenterazine to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

In certain embodiments, the compounds of formula (I) may be used to quantify coelenterazine. In some embodiments, a coelenterazine (e.g., a native or known coelenterazine or a compound of formula (I)) can be used as a probe of a specific biochemical activity, e.g., apoptosis or drug metabolism. In some embodiments, the coelenterazine concentration is coupled to a specific enzyme activity by a "pro-coelenterazine" or "pro-substrate" that can be acted on by the specific enzyme of interest. In some embodiments, the pro-coelenterazine is a molecule that cannot support luminescence directly when combined with a luciferase, but can be converted into coelenterazine through catalytic processing by a specific enzyme of interest. In some embodiments, the approach can be used for enzymes such as those used in drug metabolism, e.g., cytochrome P450 enzymes, monoamine oxidase, and glutathione S-transferase; and apoptosis, e.g., caspases. For example, coelenterazine (e.g., a native or known coelenterazine, or a compound of formula (I)) can be modified to contain a cleavable group, such as 6'-O-methyl. In some embodiments, when incubated with a specific cytochrome P450 enzyme, the 6'O-methyl is cleaved, and the pro-coelenterazine converted to coelenterazine, which can be detected with a luciferase. In some embodiments, the pro-coelenterazine can be combined with other components necessary to support luminescence, e.g., luminescent protein such as a luciferase, to provide a single reagent and a homogeneous assay. For example, when the reagent is added to a sample, luminescence is generated as pro-coelenterazine is converted to coelenterazine. In various embodiments, similar assays can be developed for other enzymes, small molecules, or other cellular processes that can be linked to the generation of coelenterazines from pro-coelenterazines.

In certain embodiments, the compounds of formula (I) can be used for detecting luminescence in live cells. In some embodiments, a luciferase can be expressed in cells (as a reporter or otherwise), and the cells treated with a coelenterazine (e.g., a compound of formula (I)), which will permeate cells in culture, react with the luciferase and generate luminescence. In addition to being cell permeant, the compounds of formula (I) show comparable biocompatibility to native coelenterazine in terms of cell viability. In some embodiments, the compounds of formula (I) containing chemical modifications known to increase the stability of native coelenterazine in media can be synthesized and used for more robust, live cell luciferase-based reporter assays. In still other embodiments, a sample (including cells, tissues, animals, etc.) containing a luciferase and a compound of formula (I) may be assayed using various microscopy and imaging techniques. In still other embodiments, a secretable luciferase is expressed in cells as part of a live-cell reporter system.

In certain embodiments, the compounds of formula (I) disclosed herein may be provided as part of a kit. In some embodiments, the kit may include one or more luciferases (in the form of a polypeptide, a polynucleotide, or both) and a coelenterazine, along with suitable reagents and instructions to enable a user to perform assays such as those disclosed herein. The coelenterazine may be any of the native, known, or compounds of formula (I) disclosed herein. The kit may also include one or more buffers, such as those disclosed herein.

4. Examples

Example 1. Synthesis of Common Intermediates (A, B, C)

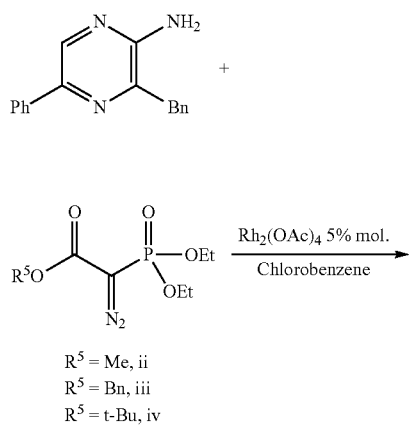

Scheme 4. Synthesis of Intermediates A-C

-continued

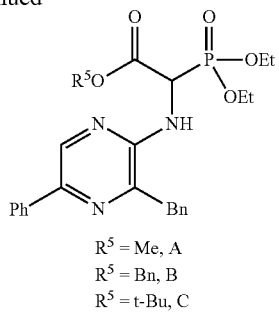

R⁵ = Me, A
R⁵ = Bn, B
R⁵ = t-Bu, C

General Procedure for the synthesis of A-C: In a 5 mL round bottom flask were placed aminopyrazine (1, 500 mg, 1.9 mmol), diazo compound (2-4, 3.83 mmol, 2 eq.), Rh$_2$(OAc)$_4$ (84.57 mg, 10 mol %) and 3 mL of chlorobenzene. The reaction mixture was heated at 100° C. for 24 hours. The progress of the reaction was monitored by LCMS. After 24 hours, the reaction reached 100% conversion. The mixture was adsorbed on celite and purified on silica column using 40% EtOAc in heptane as eluent. The desired product was isolated pure as a brown solid with a 78-90% yield. The required diazophosphonoacetates were synthesized according to Wang et al. Synlett, 2007, 11, 1683-1686.

Methyl 2-((3-benzyl-5-phenylpyrazin-2-yl)amino)-2-(diethoxyphosphoryl)acetate (A): Yield 90%; $^1$H NMR (300 MHz, CDCl$_3$) δ=8.40 (s, 1H), 7.95-7.91 (m, 2H), 7.49-7.40 (m, 2H), 7.40-7.19 (m, 6H), 5.33-5.19 (m, 2H), 4.25 (s, 2H), 4.18-3.85 (m, 4H), 3.73 (s, 3H), 1.25 (t, J=6, 3H), 1.20 (t, J=6, 3H); $^{13}$C NMR (75 MHz, cdcl3) δ=168.34, 168.32, 149.76, 149.64, 142.24, 141.72, 137.14, 136.66, 136.40, 128.85, 128.77, 128.76, 128.06, 126.96, 125.78, 63.72, 63.65, 63.63, 63.56, 53.55, 52.96, 51.61, 40.84, 16.33, 16.29, 16.25, 16.21. ESI-MS (m/z) [M+H] (C24H29N3O5P) observed 470.

Benzyl 2-((3-benzyl-5-phenylpyrazin-2-yl)amino)-2-(diethoxyphosphoryl)acetate (B): Yield 78%; $^1$H NMR (300 MHz, CDCl$_3$) δ=8.35 (s, 1H), 7.94 (d, J=7.2, 2H), 7.50-7.42 (m, 2H), 7.40-7.18 (m, 11H), 5.43-5.06 (m, 4H), 4.25 (s, 2H), 4.17-3.76 (m, 4H), 1.19 (t, J=7.1, 3H), 1.16 (t, J=7.0, 3H); $^{13}$C NMR (75 MHz, cdcl3) δ=167.70, 167.68, 149.82, 149.70, 142.27, 141.73, 137.18, 136.63, 136.39, 135.20, 128.85, 128.79, 128.77, 128.43, 128.30, 128.29, 128.07, 126.94, 125.80, 67.57, 63.72, 63.64, 63.60, 63.51, 53.96, 52.04, 40.84, 16.29, 16.24, 16.21, 16.16; ESI-MS (m/z) [M+H] (C30H32N3O5P) observed 546.

tert-Butyl 2-((3-benzyl-5-phenylpyrazin-2-yl)amino)-2-(diethoxyphosphoryl)acetate (C): Yield 83%; $^1$H NMR (300 MHz, CDCl$_3$) δ=8.41 (s, 1H), 7.95 (d, J=5.2, 2H), 7.52-7.16 (m, 8H), 5.30-5.06 (m, 2H), 4.31-4.17 (m, 2H), 4.15-3.83 (m, 4H), 1.44 (s, 9H), 1.25 (t, J=9, 3H), 1.19 (t, J=9, 3H); $^{13}$C NMR (75 MHz, cdcl3) δ=166.54, 166.52, 149.89, 149.79, 141.94, 141.60, 137.25, 136.58, 136.49, 128.80, 128.75, 127.98, 126.84, 125.73, 82.86, 63.46, 63.38, 63.29, 63.20, 54.43, 52.50, 40.75, 27.84, 16.34, 16.26; ESI-MS (m/z) [M+H] (C27H35N3O5P) observed 512.

Example 2. Method I for the Synthesis of Compounds of Formula (I)

Scheme 5. Method I

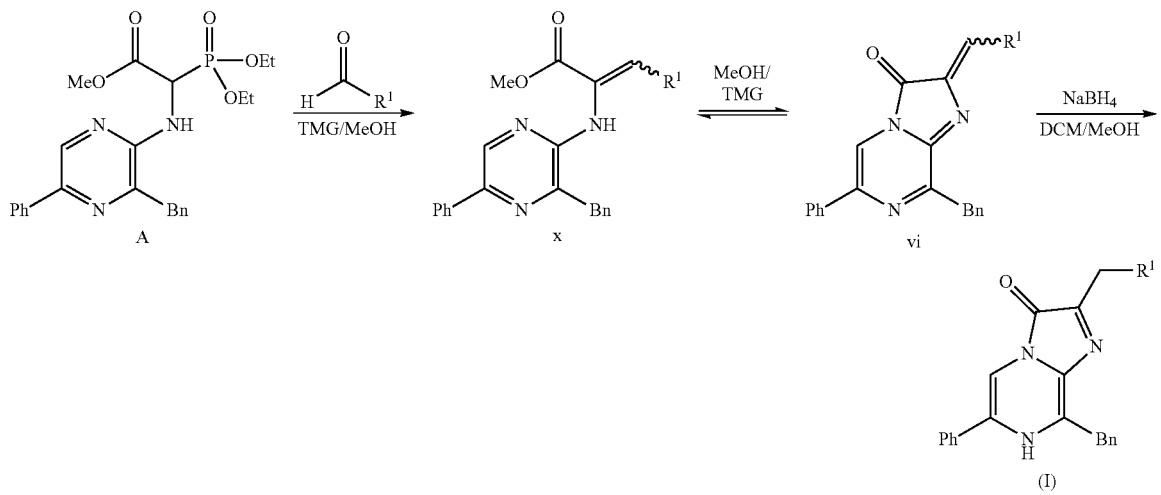

The development of methodology for synthesizing compounds of formula (I) was initiated by investigating reaction conditions for the HWE olefination shown in the scheme above. A variety of bases were screened in a HWE olefination reaction between p-fluorobenzaldehyde and compound A in THF. These initial experiments revealed that when the pKa of the base employed is less than 11 (K$_2$CO$_3$ or DIPEA), the reaction did not proceed. However, stronger nitrogenous or alkali metal bases with pKa≥12 produced complex mixtures of decomposition products. Surprisingly, employment of 1,1,3,3-tetramethylguanidine (TMG) in THF (pKa~13.6) gave rise to the olefination product in low yield (see entry 2 of Table 1).

Most aldehydes, when employed in the HWE reaction with compound A, did not exclusively provide the unsaturated ester x. Instead, x tended to cyclize to generate vi (see Scheme 5). However, these compounds were generally unstable, especially in non-protic solvents and at elevated pH. Further experiments with the solvent/base combination revealed that a wide range of protic solvents stabilize the cyclization product vi, with MeOH being preferred (see scheme below and Table 1), although pretreatment of A with TMG in methanol led to the cyclized diethylphosponate

[diethyl (8-benzyl-3-oxo-6-phenyl-3,7-dihydroimidazo[1,2-a]pyrazin-2-yl)phosphonate, compound 1].

In a model system employing p-fluorobenzaldehyde, several nitrogenous bases led to the desired cyclized product E in the reaction between A and p-fluorobenzaldehyde. In general, there was no advantage to using bases other than TMG in MeOH (Table 1).

vi was isolated as a red solid and used in the next step without further purification. Dehydrocoelenterazine vi was dissolved in 25 mL of dichloromethane and 10 mL of methanol and cooled to 0° C. To this solution, NaBH$_4$ (24.2 mg, 0.64 mmol, 3 eq.) was added, and the reaction mixture stirred at 0° C. for 30 minutes. The reaction mixture was quenched with the 50 mL of 0.1 M HCl, extracted with

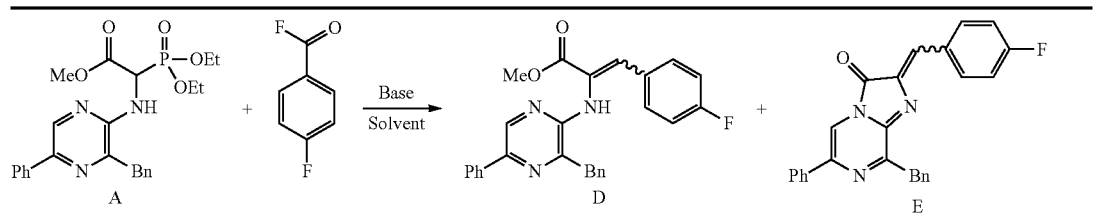

| entry | Solvent | Base | time | SM conversion % | D (%)* | E (%)* |
|---|---|---|---|---|---|---|
| 1 | Dichloromethane | TMG | 4h | 95 | 30.9 | 15 |
| 2 | THF | TMG | 4h | 100 | 10 | 37 |
| 3 | Toluene | TMG | 4h | 100 | 34 | 16 |
| 4 | Acetonitrile | TMG | 4h | 100 | 9 | 0 |
| 5 | DMF | TMG | 4h | 100 | 5 | 0 |
| 6 | Pyridine | TMG | 4h | 100 | 12 | 0 |
| 7 | Dioxane | TMG | 4h | 79 | 43 | 31 |
| 8 | Methanol | TMG | 4h | 100 | 0 | 94 |
| 9 | Methanol | DBU | 4h | 100 | 0 | 79 |
| 10 | Methanol | t-Bu-TMG | 4h | 100 | 0 | 97 |
| 11 | Methanol | TBD | 4h | 100 | 0 | 77 |
| 12 | Methanol | MeTBD | 4h | 100 | 0 | 56 |
| 13 | Ethanol | TMG | 4h | 100 | 0 | 70 |
| 14 | Ethylene glycol | TMG | 4h | 100 | 11 | 78 |
| 15 | Butanol | TMG | 4h | 100 | 17 | 28 |
| 16 | isopropanol | TMG | 4h | 100 | 5 | 24 |

Acronyms of bases and solvents used in the screening of the reaction conditions: TMG — 1,1,3,3-Tetramethylguanidine; DBU — 1,8-Diazabicycloundec-7-ene; t-BuTMG — 2-tert-Butyl-1,1,3,3- tetramethylguanidine; TBD — 1,5,7-Triazabicyclo[4.4.0]dec-5-ene; MeTBD — 7-Methyl-1,5,7- triazabicyclo[4.4.0]dec-5-ene;
*Yields of the products D and E were obtained through integration of the LCMS traces of the corresponding reaction mixtures. Conditions: room temperature, 10 mg of A, solvent (4 mL), TMG (3 eq.), 3 eq. 4-fluorobenzaldehyde aldehyde It was surmised that in the reaction between A and p-fluorobenzaldehyde, the product ratio of D and E was determined by an equilibrium established in the TMG-methanol solution, and the instability of E under these conditions led to a complete decay of the reaction components within 24 hours. Individually isolated D and E re-exposed to the reaction conditions provided similar ratios of D and E. Furthermore, when the reaction was carried out in n-butanol, similar ratios of D and E were generated, but the n-Bu-ester ($R^5$=n-Bu) also formed. Therefore, for the widest scope of substrates, methanol as solvent provided reliable access to E. Typically, synthesis of E in methanol required less than 4 h and proceeded in good yield if the reaction was quenched before significant decomposition of E was observed.

General procedure for Method I: In a 20 mL vial was placed methyl 2-((3-benzyl-5-phenylpyrazin-2-yl)amino)-2-(diethoxyphosphoryl)acetate (A) (100 mg, 0.21 mmol, 1 eq.), aldehyde (0.23 mmol, 1.1 eq.), and 12 mL of methanol. To that solution, 1,1,3,3-tetramethylguanidine (74 mg, 0.64 mmol, 3 eq.) was added. The reaction mixture was stirred at room temperature until it reached maximum conversion (2-6 hours). The progress of the reaction was monitored by LCMS. The mixture was poured into water, extracted with ethyl acetate, and dried over MgSO$_4$. The drying agent was filtered off, and the solvent was concentrated under reduced pressure. The residue was subjected to flash chromatography on silica gel using dichloromethane as eluent. The corresponding dehydrocoelenterazine with the general structure vi was isolated as a red solid and used in the next step without further purification.

dichloromethane, and dried over MgSO$_4$. The drying agent was filtered off, the solvent was concentrated under reduced pressure, and the residue was purified on silica gel using dichloromethane/methanol as eluent. The target coelenterazine analogue was isolated pure as a yellow solid and dried on high vacuum.

The following compounds were made using common intermediate A and the general procedure of Method I above. Yields were calculated for the 2 step process starting from intermediate A.

| compound | $R^1$ | Yield (%) | MS [M + H] |
|---|---|---|---|
| 2 | 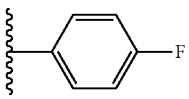 | 63 | 410 |
| 3 | 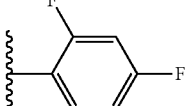 | 85 | 428 |

25
-continued
| compound | R¹ | Yield (%) | MS [M + H] |
|---|---|---|---|
| 4 | 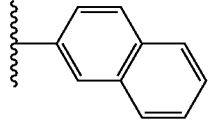 [SMILES: *c1ccc2ccccc2c1] | 59 | 442 |
| 5 | 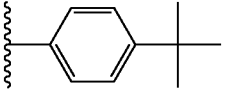 [SMILES: *c1ccc(C(C)(C)C)cc1] | 60 | 448 |
| 6 | 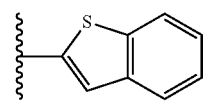 [SMILES: *c1cc2ccccc2s1] | 45 | 448 |
| 7 | 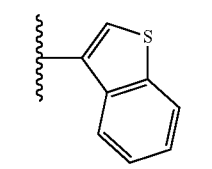 | 72 | 448 |
| 8 | 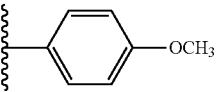 | 37 | 422 |
| 9 | 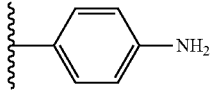 | 18 | 407 |
| 10 | 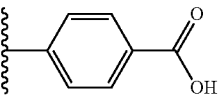 [SMILES: *c1ccc(C(=O)O)cc1] | 20 | 436 |
| 11 | 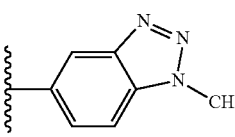 | 32 | 447 |
| 12 | 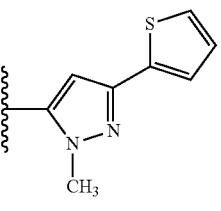 [SMILES: *c1cc(-c2cccs2)nn1C] | 36 | 478 |
| 13 | 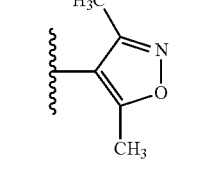 | 56 | 411 |
26
-continued
| compound | R¹ | Yield (%) | MS [M + H] |
|---|---|---|---|
| 14 | 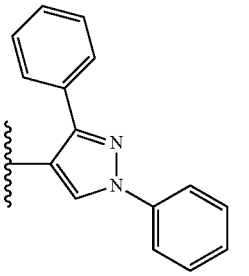 [SMILES: *c1cn(-c2ccccc2)nc1-c1ccccc1] | 47 | 534 |
| 15 | 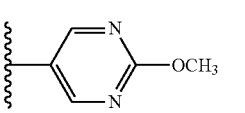 | 39 | 424 |
| 16 | 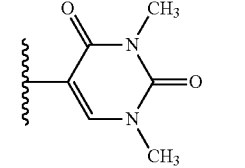 [SMILES: *c1cn(C)c(=O)n(C)c1=O] | 45 | 454 |
| 17 | 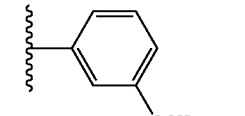 | 37 | 422 |
| 18 | 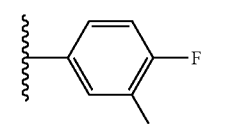 | 21 | 440 |
| 19 | 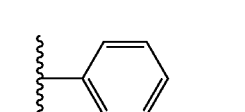 | 9 | 408 |
| 20 | 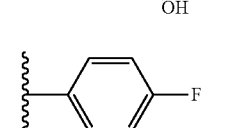 | 15 | 426 |
| 21 | 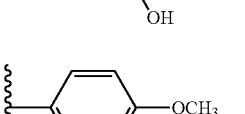 | 32 | 440 |
| 22 | 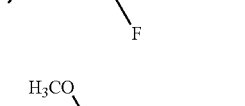 | 36 | 440 |

-continued

| compound | R¹ | Yield (%) | MS [M + H] |
|---|---|---|---|
| 23 | 3-(NHBoc)phenyl | 20 | 507 |
| 24 | 5-methoxythiophen-2-yl | 31 | 428 |
| 25 | 3-aminophenyl | 87 | 407 |
| 26 | biphenyl-4-yl | 37 | 468 |
| 27 | 2H-chromen-3-yl | 40 | 446 |
| 28 | dibenzofuran-4-yl | 26 | 482 |
| 29 | (E)-styryl | 7 | 418 |
| 30 | 4-(NHBoc)phenyl | 43 | 507 |
| 31 | 4-allyloxy-3-methoxyphenyl | 48 | 478 |
| 32 | 4-hydroxy-3-methoxyphenyl | 63 | 438 |

-continued

| compound | R¹ | Yield (%) | MS [M + H] |
|---|---|---|---|
| 33 | 5-((4-methyl-4H-1,2,4-triazol-3-yl)thio)furan-2-yl | 7 | 495 |
| 34 | 5-(pyridin-2-yl)thiophen-2-yl | 13 | 475 |
| 35 | undecan-2-yl | 18 | 470 |
| 36 | pyridin-4-yl | 4 | 393 |
| 37 | 5-cyclohexylthiophen-2-yl | 5 | 480 |
| 38 | 2,2'-bithiophen-5-yl | 6 | 480 |
| 39 | 5-isobutylthiophen-2-yl | 11 | 454 |
| 40 | 5-(1-methyl-5-(trifluoromethyl)-1H-pyrazol-3-yl)thiophen-2-yl | 7 | 546 |
| 41 | 5-(trifluoromethyl)furan-2-yl | 11 | 450 |
| 42 | 5-(methoxymethyl)furan-2-yl | 31 | 426 |
| 43 | perfluorophenyl | 10 | 482 |

-continued

| compound | R¹ | Yield (%) | MS [M + H] |
|---|---|---|---|
| 44 | 3,5-bis(trifluoromethyl)phenyl | 10 | 528 |
| 45 | 5-chloro-1-methyl-3-(trifluoromethyl)-1H-pyrazol-4-yl | 5 | 498 |
| 46 | 5-methylfuran-2-yl | 13 | 396 |
| 47 | 3-carboxyphenyl | 43 | 436 |
| 48 | 3-(aminomethyl)phenyl | 29 | 421 |
| 49 | 3-(methylsulfonamido)phenyl | 8 | 485 |
| 50 | 4-methoxy-3-(methoxymethyl)phenyl | 21 | 466 |
| 51 | 3-(dimethylamino)phenyl | 29 | 435 |
| 52 | 5-(methoxymethyl)thiophen-2-yl | 27 | 442 |

-continued

| compound | R¹ | Yield (%) | MS [M + H] |
|---|---|---|---|
| 53 | 3-(methoxymethyl)phenyl | 27 | 436 |
| 54 | 3-(hydroxymethyl)phenyl | 27 | 422 |
| 55 | 3,6-dimethylthieno[3,2-b]thiophen-2-yl | 7 | 482 |
| 56 | 2-(propylthio)pyrimidin-5-yl | 36 | 468 |
| 57 | 3,4-dimethoxyphenyl | 25 | 452 |
| 58 | 3-(methylthio)phenyl | 37 | 438 |
| 59 | benzo[d][1,3]dioxol-5-yl | 24 | 436 |
| 60 | 3-((dimethylamino)oxy)phenyl | 19 | 449 |

| compound | R¹ | Yield (%) | MS [M + H] |
|---|---|---|---|
| 61 | 3-(ethoxy)phenyl | 45 | 436 |
| 62 | 3-(2-methoxyethoxy)phenyl | 30 | 466 |

Example 3. Modification of Method I for the Synthesis of Compounds of Formula (I)

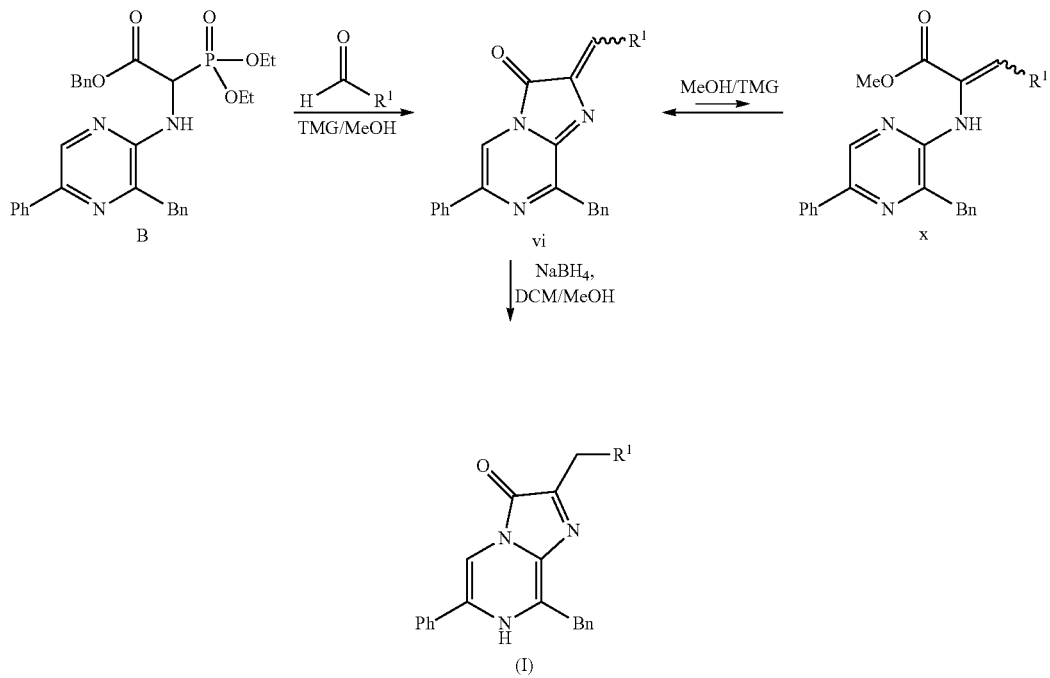

Scheme 6. Modified Method I

Further investigation of Method I showed that the use of intermediate B was advantageous in cases where the equilibrium between the cyclized and uncyclized olefin intermediate is slow. After the olefination reaction was complete, vi quickly formed, and the uncyclized intermediate was not detected in the reaction mixture. However, vi did undergo ring opening by methoxide attack, affording x. To avoid formation of x, the reaction was halted after 100% conversion of B (10-20 minutes). Reduction of vi afforded the compound of formula (I) smoothly, though. This two-step process can be completed within 10-20 minutes. Moreover, yields of challenging substrates can be increased.

Throughout these studies it was observed that electron withdrawing substituents at the R¹ position tend to favor the formation of closed form vi. This was taken advantage of and modified Method I was used to prepare compounds of formula (I) containing pyridinyl groups at the R¹ position.

The following compounds were made in an analogous fashion using common intermediate B and the general procedure of Method I in Example 2. Yields were calculated for the 2 step process starting from intermediate B.

| compound | R¹ | Yield (%) | MS [M + H] |
|---|---|---|---|
| 63 | 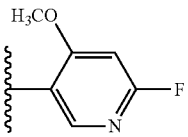 [SMILES: *c1ccc(F)cc1OC] Mixture of regioisomers | 33 | 441 |
| 64 | 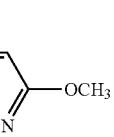 | 13.7 | 393 |
| 65 | 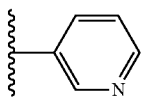 | 27.9 | 429 |
| 66 | 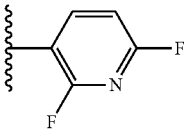 [SMILES: *c1ccc(F)nc1F] | 35.9 | 411 |
| 67 | 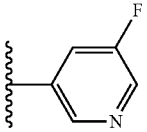 [SMILES: *c1cncc(F)c1] | 29.2 | 411 |
| 68 | 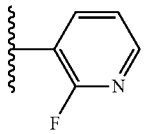 [SMILES: *c1cccnc1F] | 16 | 411 |
| 69 | 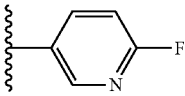 [SMILES: *c1ccc(F)nc1] | 28 | 427 |
| 70 | 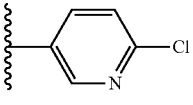 [SMILES: *c1ccc(Cl)nc1] | 25.4 | 471 |
| 71 | 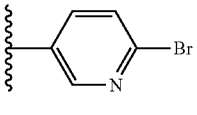 | 72.1 | 423 |
| 72 | 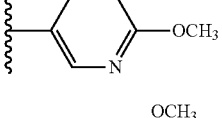 | 34.8 | 423 |
| 73 | 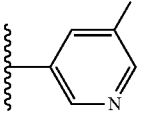 | 42 | 453 |
| 74 | 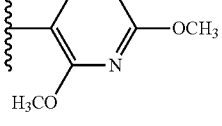 | 32.2 | 457 |

-continued

| compound | R¹ | Yield (%) | MS [M + H] |
|---|---|---|---|
| 75 | 2,6-dichloropyridin-3-yl | 25.9 | 461 |
| 76 | 6-methylpyridin-3-yl | 35.1 | 407 |
| 77 | 6-(dimethylamino)pyridin-3-yl | 27.5 | 436 |

Example 4. Methods II and III for the Synthesis of Compounds of Formula (I)

Method I is a convenient and fast method with short reaction times that enables access to a variety of compounds of formula (I). However, many compounds of formula (I) containing electron deficient aromatic rings or reactive heterocyclic rings at the R¹ position could not be made by Method I. In some cases, olefination and subsequent cyclization were slow, and significant decomposition of the products was observed. On the other hand, electron rich aldehydes tended to have low conversion rates in the HWE olefination reaction which led to the formation of significant amounts of 1, an unproductive intermediate (see Example 2).

To circumvent these challenges, two alternate routes were developed. Utilization of C prevented cyclization to the imidazolinone ring during the HWE reaction, providing only unsaturated ester vii. Subsequent treatment with TFA generated unsaturated acid ix, which was converted to the compound of formula (I) through a two-step cyclization and reduction sequence (Method II). In this method, vii was typically isolated in excellent yield. Following the hydrolysis approach, Method II avoids exposing sensitive intermediates to high pH conditions. Thus, in cases when the product ix is stable to TFA treatment, Method II afforded compounds of formula (I) with higher yields than Method I, although the process was lengthier.

Scheme 7. Method II

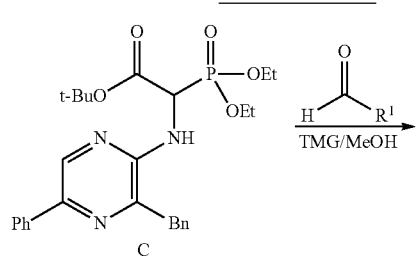

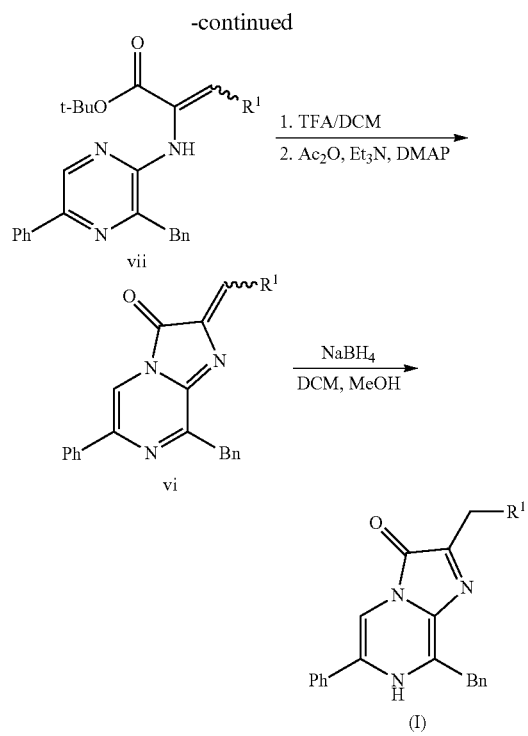

General procedure for Method II: In a 20 mL vial was placed tert-butyl 2-((3-benzyl-5-phenylpyrazin-2-yl)amino)-2-(diethoxyphosphoryl)acetate (C) (200 mg, 0.39 mmol, 1 eq.), aldehyde (0.43 mmol, 1.1 eq.), and 15 mL of methanol. To that solution, 1,1,3,3-tetramethylguanidine (135 mg, 1.2 mmol, 3 eq.) was added, and the reaction mixture was stirred at room temperature for 2 hours. The progress of the reaction was monitored by LCMS. The reaction mixture was poured into water extracted with ethyl acetate and dried over MgSO₄. The drying agent was filtered off, the solvent was concentrated under reduced pressure, and the product with the general structure vii was used in the next step without further purification.

To a solution of vii in dichloromethane (5 mL), trifluoroacetic acid (2 mL) was added. The reaction mixture stirred at room temperature for 4 hours. The progress of the reaction was monitored by LCMS. After the reaction was complete, all volatiles were removed under reduced pressure, and the residue was dried under high vacuum. The resulting unsaturated acid was dissolved in THF (10 mL), and to this solution, acetic anhydride (398 mg, 3.9 mmol, 10 eq.), triethylamine (395 mg, 3.9 mmol, 10 eq.) and DMAP (4.8 mg, 0.039 mmol, 0.1 eq.) were added. The reaction mixture stirred at room temperature for 30 min and poured in the water, then extracted with dichloromethane, and dried over MgSO$_4$. The drying agent was filtered off, and the solvent was concentrated under reduced pressure. The residue was subjected to a flash chromatography on silica gel using dichloromethane as eluent. The corresponding dehydrocoelenterazine with the general structure vi was isolated as red solid and used in the next step without further purification.

Dehydrocoelenterazine vi was dissolved in 25 mL of dichloromethane and 10 mL of methanol and cooled to 0° C. To this solution, NaBH$_4$ (44.26 mg, 1.2 mmol, 3 eq.) was added, and the reaction mixture stirred at 0° C. for 30 minutes. The reaction mixture was quenched with 100 mL of 0.1 M HCl, extracted with dichloromethane, and dried over MgSO$_4$. The drying agent was filtered off, the solvent was concentrated under reduced pressure, and the residue was purified on silica gel using dichloromethane/methanol as eluent. The target coelenterazine analogue of formula (I) was isolated pure as a yellow solid and dried on high vacuum.

Method III is a second alternative that bypasses all potentially unstable synthetic intermediates. Hydrogenation of unsaturated ester vii, which was achieved in the presence of Wilkinson's catalyst under elevated pressure of hydrogen, yielded intermediate viii, which was typically easy to isolate and purify. TFA treatment of viii, followed by intramolecular cyclization of the corresponding acid using carbonyl diimidazole (CDI) afforded the compound of formula (I). Method III employs mild reaction conditions and avoids oxygen and moisture sensitive reaction intermediates; it is suitable both for scale-up and preparation of coelenterazine analogue containing sensitive functional groups. However, high pressure and prolonged reaction times are required.

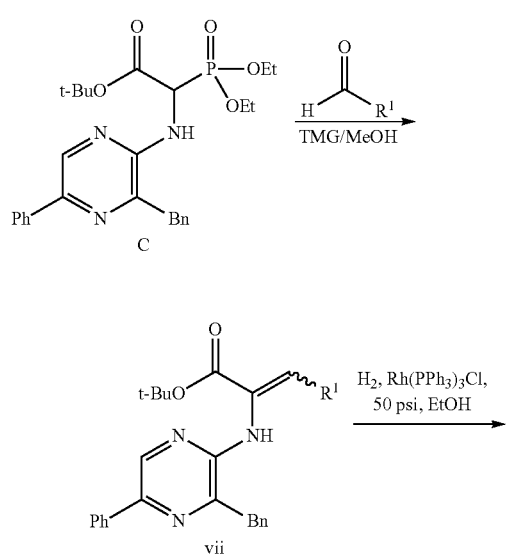

Scheme 8. Method III

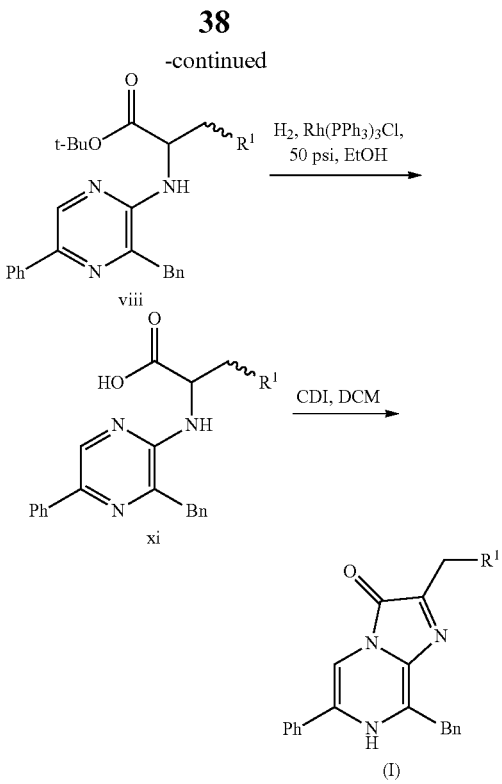

General procedure for Method III: In a 20 mL vial was placed tert-butyl 2-((3-benzyl-5-phenylpyrazin-2-yl)amino)-2-(diethoxyphosphoryl)acetate (C) (200 mg, 0.39 mmol, 1 eq.), aldehyde (0.43 mmol, 1.1 eq.), and 15 mL of methanol. To that solution, 1,1,3,3-tetramethylguanidine (135 mg, 1.2 mmol, 3 eq.) was added, and the reaction mixture was stirred at room temperature for 1-2 hours. The progress of the reaction was monitored by LCMS. After the reaction was complete, the mixture was poured into water, extracted with ethyl acetate, and dried over MgSO$_4$. The drying agent was filtered off, and the solvent was concentrated under reduced pressure. The residue was purified using flash chromatography on silica gel with heptane/ethyl acetate as eluent and target compound vii was isolated as colorless oil.

In a parr-shaker reactor flask was placed tert-butyl 2-(3-benzyl-5-phenylpyrazin-2-ylamino)-acrylate derivative vii (0.3 mmol, 1 eq.), Rh(PPh$_3$)$_3$Cl (0.03 mmol, 0.1 eq.), and 50 mL of ethanol. The reactor was charged with H$_2$ (50 psi) and shaken for 20 hours at room temperature. The reaction was monitored by LCMS. Then, all volatiles were removed under reduced pressure, and the residue was subjected to flash chromatography on silica gel using heptane/ethylacetate as eluent. The reduced aminopirazine derivative viii was isolated pure as colorless oil.

Compound viii (0.25 mmol, 1 eq.) was dissolved in dichloromethane (5 mL), and to this solution, trifluoroacetic acid (2 mL) was added. The reaction mixture stirred at room temperature for 12 hours. The progress of the reaction was monitored by LCMS. After the reaction was complete, all volatiles were removed under reduced pressure, and the residue was co-evaporated 3 times with 10 mL of toluene to remove all TFA and provide compound xi. After drying under high vacuum, compound xi was dissolved in dichloromethane (15 mL), and to this solution was added carbodiimidazole (CDI) (122 mg, 0.75 mmol, 3 eq.). The reaction mixture stirred at room temperature for 20 minutes and then poured into 0.01 M HCl (50 mL), extracted with dichloromethane, and dried over MgSO₄. The drying agent was filtered off, and the solvent was concentrated under reduced pressure. The residue was subjected to a flash chromatography on silica gel using dichloromethane/methanol as eluent. The corresponding coelenterazine of formula (I) was isolated pure as yellow solid.

The following exemplary intermediates were isolated and characterized in the employment of Method III:

tert-Butyl (E)-2-((3-benzyl-5-phenylpyrazin-2-yl)amino)-3-(3-cyanophenyl)acrylate

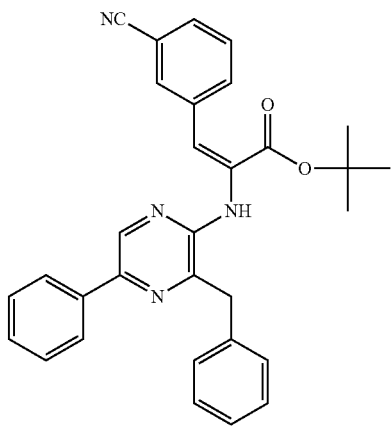 [SMILES: CC(C)(C)OC(=O)/C(=C\c1cccc(C#N)c1)Nc1ncc(-c2ccccc2)nc1Cc1ccccc1]

$^1$H NMR (300 MHz, CDCl₃) δ=10.03 (s, 1H), 8.31 (s, 1H), 8.15 (td, J=0.6, 1.6, 1H), 8.12-8.08 (m, 1H), 7.96-7.87 (m, 2H), 7.68 (t, J=7.7, 1H), 7.51-7.35 (m, 4H), 7.33-7.23 (m, 3H), 7.21-7.07 (m, 1H), 6.98 (s, 1H), 6.34 (s, 1H), 4.30 (s, 2H), 1.46 (s, 9H); $^{13}$C NMR (75 MHz, CDCl₃) δ=189.91, 164.29, 148.16, 143.74, 142.89, 137.18, 136.85, 136.79, 136.76, 136.62, 136.13, 133.27, 133.12, 132.29, 132.23, 131.08, 130.23, 130.09, 129.20, 129.12, 128.83, 128.54, 128.49, 127.41, 126.02, 121.99, 118.39, 117.54, 113.68, 112.55, 104.99, 82.43, 41.15, 27.89; ESI-MS (m/z) [M+H] (C31H29N4O2) observed 489.

tert-Butyl 2-((3-benzyl-5-phenylpyrazin-2-yl)amino)-3-(3-cyanophenyl)propanoate

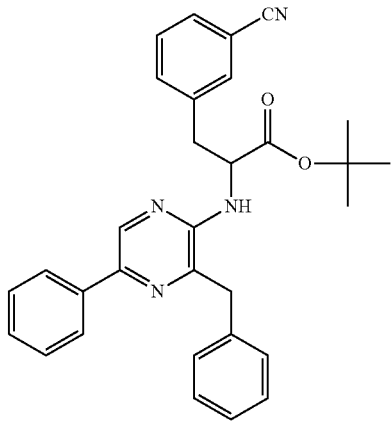 [SMILES: CC(C)(C)OC(=O)C(Cc1cccc(C#N)c1)Nc1ncc(-c2ccccc2)nc1Cc1ccccc1]

$^1$H NMR (300 MHz, CDCl₃) δ=8.40 (s, 1H), 7.98-7.92 (m, 2H), 7.50-7.43 (m, 3H), 7.38-7.23 (m, 7H), 7.22-7.18 (m, 1H), 7.11 (dt, J=1.5, 7.8, 1H), 5.02 (d, J=6.8, 1H), 4.93-4.79 (m, 1H), 4.15 (q, J=15.3, 3H), 3.10 (ddd, J=5.8, 13.9, 34.0, 2H), 1.38 (s, 9H); $^{13}$C NMR (75 MHz, CDCl₃) δ=170.81, 150.01, 141.21, 141.14, 138.34, 137.35, 136.79, 136.45, 133.91, 132.94, 130.36, 128.93, 128.91, 128.77, 128.58, 127.88, 127.03, 125.66, 118.72, 112.15, 82.50, 55.09, 40.94, 37.46, 27.96; ESI-MS (m/z) [M+H] (C31H31N4O2) observed 491.

tert-Butyl (E)-2-((3-benzyl-5-phenylpyrazin-2-yl)amino)-3-(1,2,3-thiadiazol-5-yl)acrylate

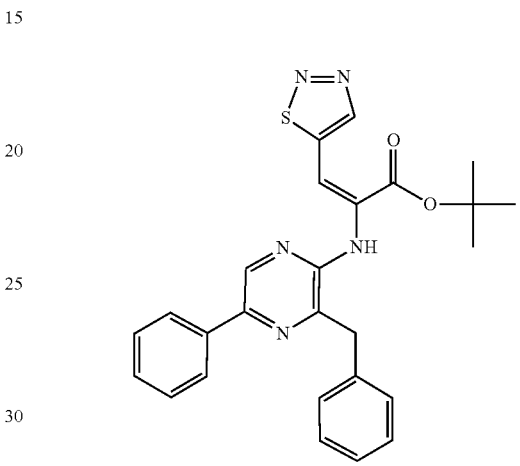

$^1$H NMR (300 MHz, CDCl₃) δ=9.45 (s, 1H), 8.51 (s, 1H), 8.27 (s, 1H), 8.03-7.96 (m, 2H), 7.52-7.45 (m, 4H), 7.43-7.31 (m, 3H), 7.30-7.22 (m, 1H), 6.70 (s, 1H), 4.43 (s, 2H), 1.48 (s, 9H); $^{13}$C NMR (75 MHz, CDCl₃) δ=164.35, 159.03, 147.85, 144.44, 143.61, 136.90, 136.87, 136.42, 135.80, 133.05, 129.07, 128.85, 128.74, 128.54, 126.81, 126.09, 104.18, 82.10, 40.34, 27.87; ESI-MS (m/z) [M+H] (C26H26N5O2S) observed 472 tert-Butyl 2-((3-benzyl-5-phenylpyrazin-2-yl)amino)-3-(1,2,3-thiadiazol-5-yl)propanoate

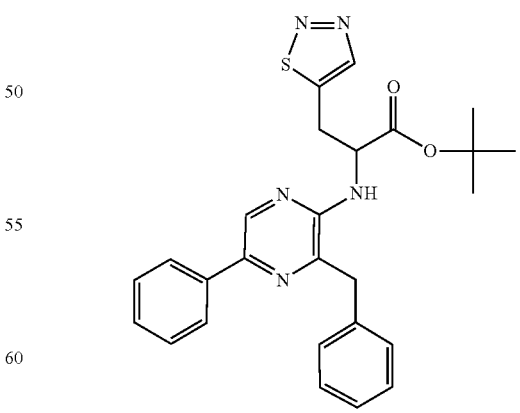

$^1$H NMR (300 MHz, CDCl₃) δ=8.42 (s, 1H), 7.99-7.93 (m, 2H), 7.51-7.42 (m, 3H), 7.41-7.23 (m, 6H), 5.41 (d, J=6.6, 1H), 5.00 (dt, J=5.0, 6.5, 1H), 4.19 (dd, J=15.2, 58.4, 2H), 3.82-3.62 (m, 2H), 1.36 (s, 9H); $^{13}$C NMR (75 MHz,

CDCl$_3$) δ=170.52, 158.41, 149.87, 141.26, 141.12, 137.38, 136.91, 136.87, 132.95, 129.02, 128.81, 128.78, 127.88, 127.01, 125.65, 82.60, 53.92, 40.98, 30.06, 27.83; ESI-MS (m/z) [M+H] (C26H28N5O2S) observed 474.

The following compounds were made by Methods II and III described above. Yields were calculated for the 4 step process starting from intermediate C.

| Compound | R$^1$ | Method | Yield (%) | MS [M + H] |
|---|---|---|---|---|
| 78 | (2,4,5-trifluorophenyl) | II | 78% | 446 |
| 79 | (3-cyanophenyl) | III | 30% | 417 |
| 80 | (imidazo[2,1-b]thiazolyl) | II | 32% | 438 |
| 81 | (5-(morpholinomethyl)furan-2-yl) | II | 25% | 481 |
| 82 | (1,2,3-thiadiazol-5-yl) | III | 17% | 400 |
| 83[a] | (3-acetyl-benzothiazol-2-ylidene) | II | 6 | 491 |
| 84 | (pyrazinyl) | II | 12 | 394 |
| 85 | (1-methyl-pyrrolo-thiophene) | II | 7 | 451 |
| 86[a] | (styryl) | II | 10 | 404 |

[a]compounds were made by Method II, but excluding the final reduction step with NaBH$_4$ Thus, having established multiple synthetic methodologies, the scope and utility of these methods were demonstrated by synthesizing compounds of formula (I) with a wide variety of substituents at the R$^1$ position. As shown above, aromatic groups with electron-withdrawing substituents, aromatic groups with electron-donating substituents, sterically demanding groups, and polar heterocyclic motifs were all amenable to synthesis using one of these new methods.

Example 5. Luminescent Properties

Luminescence Assay Procedure: Each compound to be screened was dissolved in DMSO (5 mM) and then further diluted to 100 uM in NANO-GLOR Luciferase Assay Buffer. Each diluted substrate was then combined in equal volumes with purified NanoLuc® Luciferase diluted into $CO_2$ independent media+10% FBS. Initial light output for each substrate was measured in a GloMax®-Multi+ luminometer three minutes after substrate addition and then at five minute intervals as a means to determine signal half-life.

A subset of the synthesized coelenterazine analogues (compounds of formula (I)) were evaluated for their suitability as luciferase substrates. NANOLUC® luciferase was employed for the screening because it is a small (19 kDa), stable, and particularly bright enzyme. Table 2 demonstrates that relative light unit (RLUs) and half-life data (ratios in comparison to native coelenterazine) indicated that moderately electron-donating and electron-withdrawing functionalities were well tolerated. A variety of pyridinyl groups were also tolerated with a significant number demonstrating superior performance to coelenterazine. Overall, a significant number of analogues were superior to coelenterazine in generating luminescence.

TABLE 2

| Compound | I | Half-life |
|---|---|---|
| coelenterazine | 1 | 1 |
| 1 | — | — |
| 2 | 40 | 0.16 |
| 3 | 38.75 | 0.23 |
| 4 | 9.166 | 0.72 |
| 5 | 3.875 | 0.43 |
| 6 | 13.75 | 0.33 |
| 7 | 4.166 | 0.52 |
| 8 | 23.333 | 0.38 |
| 9 | 1.041 | 0.93 |
| 10 | 0.142 | 1.02 |
| 11 | 0.3 | 1.04 |
| 12 | 0.192 | 0.57 |
| 13 | 0.583 | 2.64 |
| 14 | 0.042 | 2.15 |
| 15 | 0.583 | 0.88 |
| 16 | 0.0042 | 0.005 |
| 64 | 2.75 | 3.03 |
| 65 | 10.833 | 0.62 |
| 66 | 1.625 | 0.98 |
| 67 | 4.583 | 1.14 |
| 68 | 12.916 | 0.93 |
| 69 | 7.5 | 0.35 |
| 70 | 5 | 0.19 |
| 71 | 27.083 | 0.14 |
| 72 | 1.208 | 0.88 |
| 73 | 6.666 | 0.93 |
| 74 | 3 | 1.09 |
| 75 | 0.958 | 0.57 |
| 76 | 1.666 | 1.14 |
| 77 | 1.75 | 0.57 |
| 78 | 8.75 | 0.43 |
| 79 | 13.87 | 0.52 |
| 80 | 2.166 | 1.62 |
| 81 | 0.246 | 1.19 |
| 82 | 5.416 | 1.19 |

The compounds of formula (I) were also evaluated for their ability to be luciferase substrates in an additional assay. In this assay, the analogues were compared to a known coelenterazine analogue, 8-benzyl-2-(furan-2-ylmethyl)-6-phenylimidazo[1,2-a]pyrazin-3(7H)-one (C-1), which is known to be superior to coelenterazine as a luciferase substrate. Table 3 demonstrates that a significant number of the analogues were well tolerated and performed similarly to or better than 8-benzyl-2-(furan-2-ylmethyl)-6-phenylimidazo[1,2-a]pyrazin-3(7H)-one.

TABLE 3

| Compound | RLU (@100 uM) | half-life (@100 uM) | Km |
|---|---|---|---|
| C-1 | 1 | 1 | 1 |
| 1 | 0.00048 | 0.4 | 3 |
| 2 | 0.96 | 0.32 | 2.68 |
| 3 | 0.93 | 0.45 | 2.47 |
| 4 | 0.22 | 1.4 | 4.2 |
| 5 | 0.093 | 0.83 | 6.4 |
| 6 | 0.33 | 0.646 | 3.7 |
| 7 | 0.1 | 1 | 3 |
| 8 | 0.56 | 0.73 | 1.83 |
| 9 | 0.025 | 1.8 | 5.57 |
| 10 | 0.0034 | 1.96 | 7.4 |
| 11 | 0.0072 | 2 | 3.3 |
| 12 | 0.0046 | 1.1 | 3.4 |
| 13 | 0.014 | 5.1 | 4.96 |
| 14 | 0.001 |  | 14 |
| 15 | 0.014 | 1.7 | 4.3 |
| 16 | 0.0001 | 0.01 | 3.7 |
| 17 | 0.83 | 1.2 | 2.28 |
| 18 | 0.4 | 1.28 | 4.05 |
| 19 | 0.1 | 3.34 | 3.63 |
| 20 | 0.29 (75) | 1.87 (75) | 4.95 |
| 21 | 0.32 | 0.81 | 2.26 |
| 22 | 0.3 (75) | 1.79 (75) | 2.32 |
| 23 | 0.001 | 5 | 4.61 |
| 24 | 0.68 | 0.55 | 1.98 |
| 25 | 0.15 | 3.22 | 4.29 |
| 26 | 0.046 | 1.09 | 4.5 |
| 27 | 0.1 | 1.19 | 2.2 |
| 28 | 0.01 |  | 2.47 |
| 29 | 0.13 |  | 14.3 |
| 30 | 0.001 | 3.5 | 4.62 |
| 31 | 0.054 | 1.56 | 4.44 |
| 32 | 0.052 | 1.35 | 6.5 |
| 33 | 0.017 | 1.9 | 8.3 |
| 34 | 0.02 | 1.2 | 1.89 |
| 35 | 0.0005 | 4.92 | 7.5 |
| 36 | 0.0017 | N/A | 0.97 |
| 37 | 0.05 | 0.45 | 1.25 |
| 38 | 0.054 | 0.6 | 1.25 |
| 39 | 0.29 | 0.92 | 6.8 |
| 40 | 0.0042 | 0.71 | 6.2 |
| 41 | 0.82 | 0.6 | 2 |
| 42 | 0.52 | 1.3 | 4.5 |
| 43 | 0.052 | 0.56 | 3.2 |
| 44 | 0.019 | 1.1 | 8.2 |
| 45 | 0.0012 | 2.4 | 7.3 |
| 46 |  |  |  |
| 47 | 0.013 | 2.9 | 4 |
| 48 | 0.0013 | 4.4 | 11.7 |
| 49 | 0.002 | 4.4 | 4.8 |
| 50 | 0.023 | 2.2 | 4 |
| 51 | 0.49 | 1.2 | 3.2 |
| 52 | 0.45 | 1 | 2.2 |
| 53 | 0.47 | 1.6 | 2.1 |
| 54 | 0.04 | 2.8 | 3.8 |
| 55 | 0.0063 | 1.4 | 4.4 |
| 56 | 0.0098 | 0.9 | 6.1 |
| 57 | 0.063 | 1.7 | 4.5 |
| 58 | 0.47 | 1.2 | 3.2 |
| 59 | 0.72 | 0.53 | 1.7 |
| 60 | 0.00038 | 4.1 | 6.9 |
| 61 | 0.49 | 1.7 | 3.4 |
| 62 | 0.057 | 3.36 | 3.97 |

TABLE 3-continued

| Compound | RLU (@100 uM) | half-life (@100 uM) | Km |
|---|---|---|---|
| 63 | 0.28 | 0.5 | 1.6 |
| 64 | 0.066 | 5.85 | 1.82 |
| 65 | 0.26 | 1.2 | 7.1 |
| 66 | 0.039 | 1.9 | 2.8 |
| 67 | 0.11 | 2.2 | 6.7 |
| 68 | 0.31 | 1.8 | 11 |
| 69 | 0.18 | 0.68 | 3.6 |
| 70 | 0.12 | 0.37 | 3.1 |
| 71 | 0.65 | 0.28 | 1.9 |
| 72 | 0.029 | 1.7 | 3 |
| 73 | 0.16 | 1.8 | 2.7 |
| 74 | 0.072 | 2.1 | 3.4 |
| 75 | 0.023 | 1.1 | 6.5 |
| 76 | 0.04 | 2.2 | 6.3 |
| 77 | 0.042 | 1.1 | 5.8 |
| 78 | 0.21 | 0.83 | 3.8 |
| 79 | 0.33 |  | 4.06 |
| 80 | 0.052 | 3.12 | 7.1 |
| 81 | 0.0059 | 2.3 | 6.7 |
| 82 | 0.13 | 2.3 | 10 |
| 83 | 0.02 |  | 11.1 |
| 84 | 0.003 | 3.1 | 8 |
| 85 | 0.038 | 0.5 | NA |
| 86 | 0.0002 | NA | NA |

Example 6. Cell Permeability and Bioluminescent Activity

Cell Culture: HeLa and HEK293 cells were maintained in DMEM containing 0.3 mg/ml glutamine, 100 IU/ml penicillin, 100 µg/ml streptomycin, and 10% fetal calf serum at 37° C. in 5% $CO_2$. Dulbecco's modified eagle medium (DMEM), Opti-MEM, Penicillin/Streptomycin, and Trypsin-EDTA were purchased from Life Technologies (Carlsbad). Fetal calf serum (FBS) was purchased from HyClone (GE Healthcare). Microtiter plates were purchased from Corning.

Cell based luciferase assay: HEK293 cells stably expressing NANOLUC® luciferase under the control of a CMV promotor were plated in 100 l growth medium (DMEM supplemented with 10% FBS) into wells of white, TC-treated, 96-well plates at a density of 10000 cells per well and incubated for 24 h. The growth medium was then replaced with 100 µl OptiMEM containing 12.5 µM of the indicated substrate. The luminescent signal was analyzed immediately following substrate addition using a GLO-MAX® Discover multimode detection plate reader (Promega).

Figure 2:
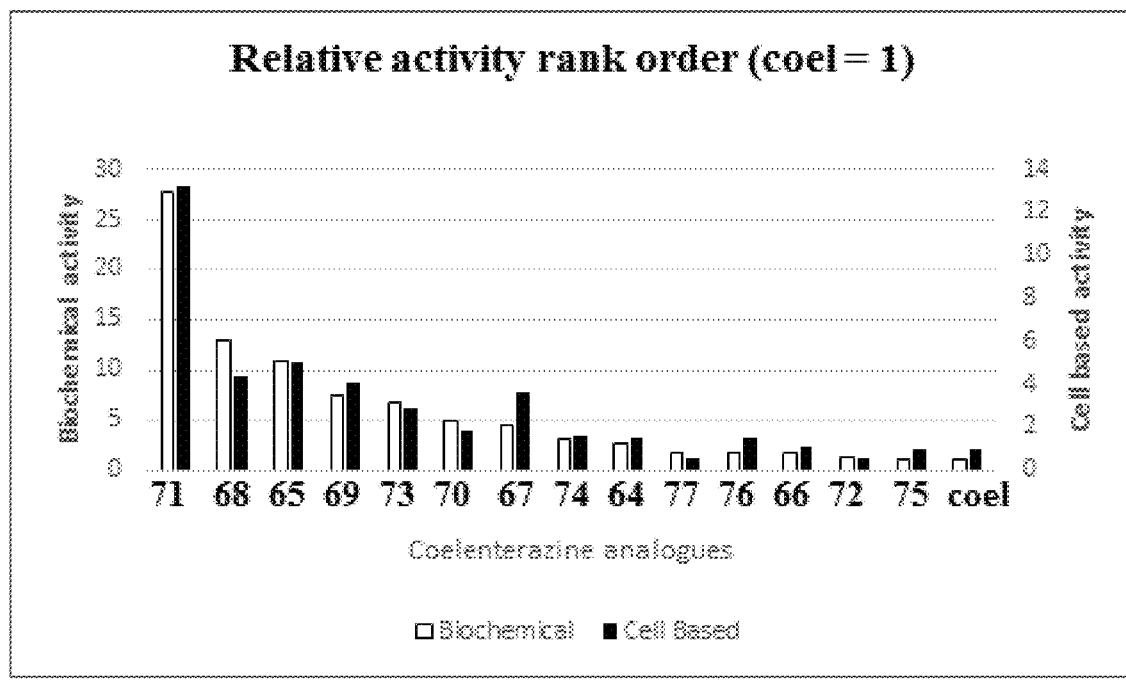
FIG. 2 is a graph depicting the rank ordering of compounds of formula (I) by signal strength relative to coelenterazine.

Cell permeability and bioluminescent activity of certain compounds (64-77) were determined in comparison to coelenterazine using HEK293 cells stably expressing NANO-LUC® luciferase (FIG. 1). A majority of the compounds tested exhibited a luminescent signal equal or stronger than with coelenterazine, and at least six showed a substantial increase (>5-fold) over coelenterazine. Furthermore, rank ordering compounds by signal strength relative to coelenterazine showed a strong correlation between the biochemical and cell-based luciferase assay (FIG. 2). Together, these results imply that the tested analogues were freely permeable across biological membranes and show good bioluminescent activity within living cells.

Example 7. Cell Viability

Cell viability assay: HEK293 or HeLa cells were plated in 100 l growth medium (DMEM supplemented with 10%

FBS) into wells of white, TC-treated, 96-well plates at a density of 10000 cells per well and incubated for 24 h. The growth medium was then replaced with 100 μl Opti-MEM medium, which contained a serial dilution of the indicated compound. Changes in cell viability were then measured after incubation for 24 h using the CELLTITER® Green cell viability assay (Promega) according to manufacturer instructions. All luminescent measurements were performed on a GLOMAX® Discover multimode plate reader (Promega).

Figure 3:
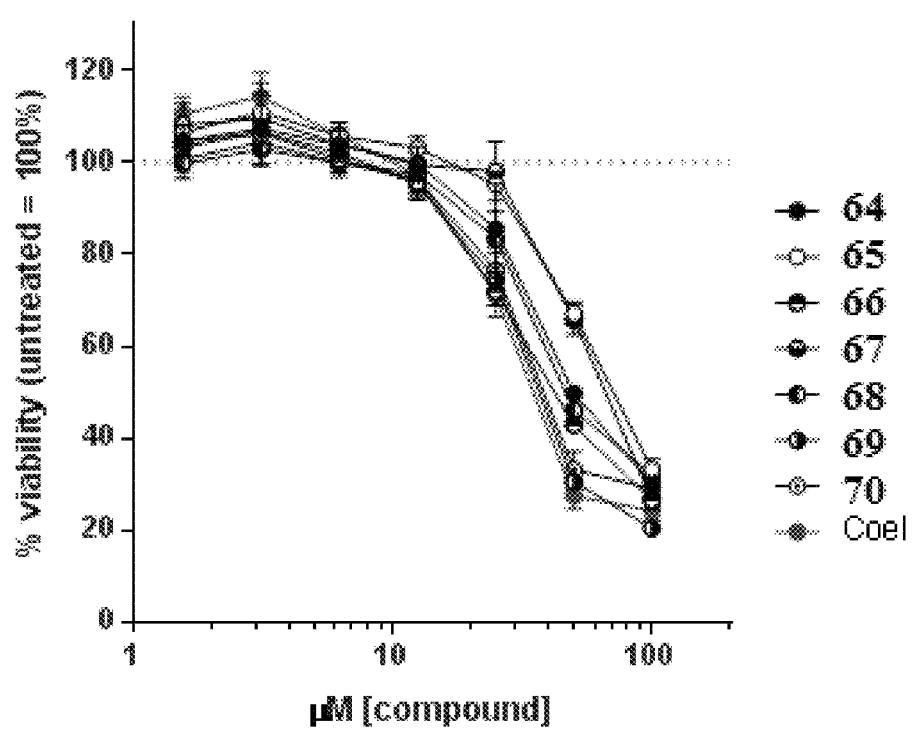
FIG. 3 and FIG. 4 are graphs depicting results of a cell viability assay employing exemplary compounds in HeLa cells.
Figure 4:
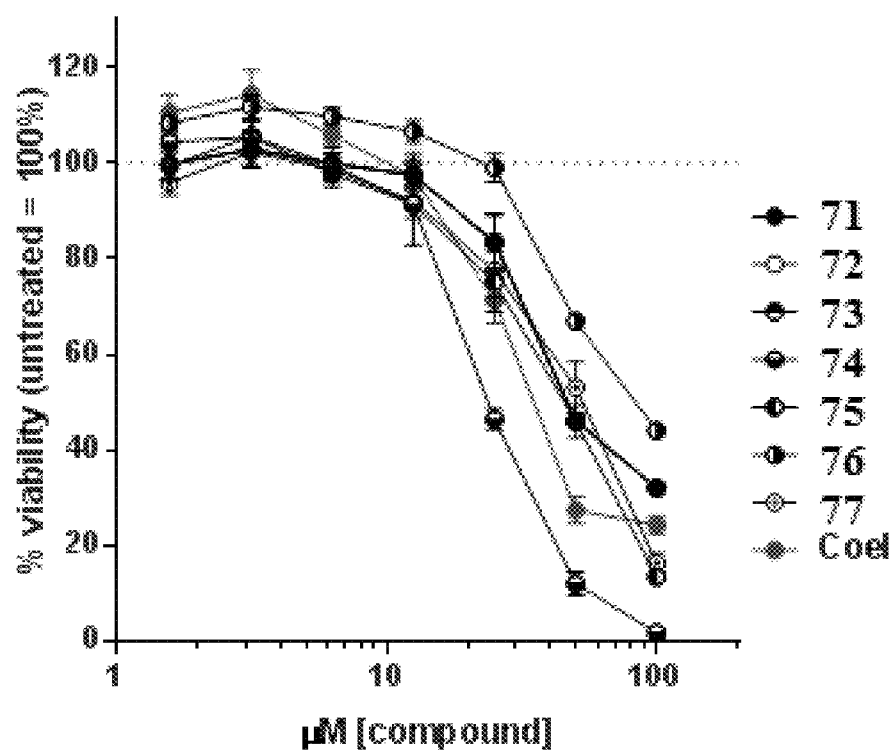
Figure 5:
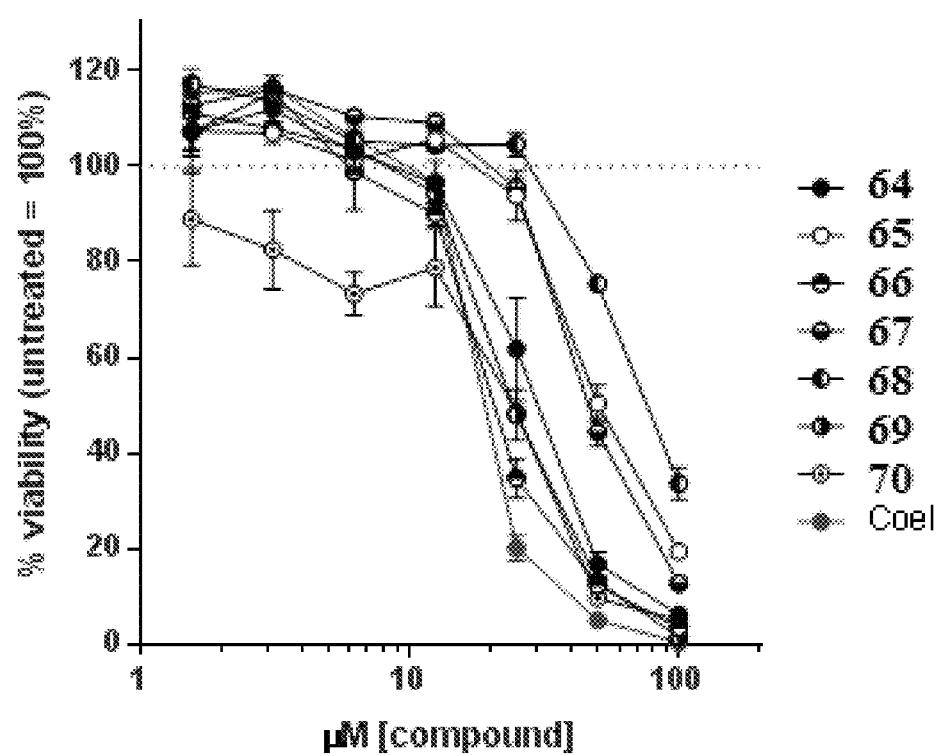
FIG. 5 and FIG. 6 are graphs depicting results of a cell viability assay employing exemplary compounds in HEK293 cells.
Figure 6:
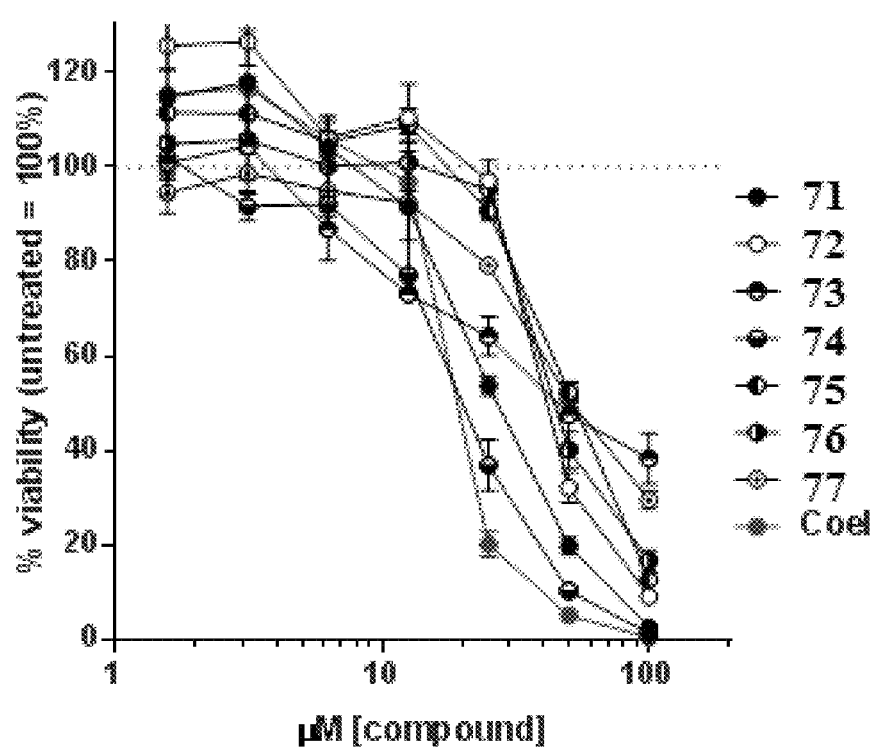

Evaluation of compound-induced cellular toxicity in HeLa (FIGS. 3 and 4) and Hek293 (FIGS. 5 and 6) cells showed no fundamental difference in the substrate toxicity pattern throughout the two different cell lines. Interestingly, fluorinated compounds 65-68 generally demonstrated reduced toxicity in both cell lines when compared to coelenterazine. In addition compound 76 also exhibited notably reduced toxicity in both cell lines, which might enable the use of higher substrate concentrations in cell based assays.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for detecting luminescence in a sample, the method comprising:
   (a) contacting a sample with a compound of formula (I):

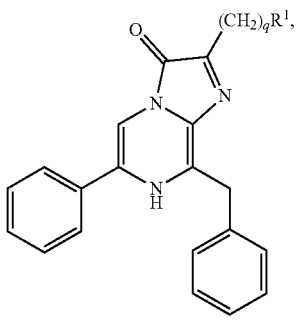

or a pharmaceutically acceptable salt or tautomer thereof,
wherein:
$R^1$ is heterocyclyl, aryl, or heteroaryl, wherein the heterocyclyl, aryl, or heteroaryl is optionally substituted with 1, 2, 3, 4, 5, 6, or 7 substituents independently selected from the group consisting of oxo, thioxo, nitro, cyano, hydroxy, alkyl, haloalkyl, hydroxyalkyl, alkoxyalkyl, aminoalkyl, alkoxyfluoroalkyl, cycloalkylalkyl, heterocyclylalkyl, arylalkyl, heteroarylalkyl, alkenyl, alkynyl, alkoxy, haloalkoxy, allyloxy, benzyloxy, aryloxy, silyloxy, sulfanyl, alkylsulfanyl, amino, alkylamino, acylamino, arylamino, sulfinylamino, sulfonylamino, acyl, carboxy, carbamate, amido, sulfinyl, sulfonyl, silyl, cycloalkyl, cycloalkenyl, heterocyclyl, aryl, and heteroaryl; and
q is 1;
with the proviso that:
$R^1$ is not selected from the group consisting of:

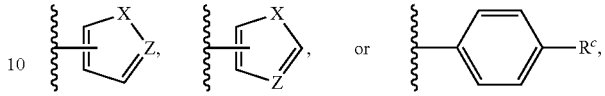

wherein:
$R^c$ is H, OH, OC(O)$C_1$-$C_7$ alkyl, or OCH$_2$OC(O) $C_1$-$C_7$ alkyl;
X is NH, N(CH$_3$), N(CH$_2$CH$_3$), S, or O; and
Z is CH or N;
(b) contacting the sample with a coelenterazine-utilizing luciferase, if it is not present in the sample; and
(c) detecting luminescence.

2. The method of claim 1, wherein
$R^1$ is chromenyl, benzodioxolyl, 1,3-dimethylpyrimidine-2,4(1H,3H)-dionyl, phenyl, naphthalenyl, pyrazolyl, furanyl, thienyl, thiazolyl, thiadiazolyl, isoxazolyl, pyridinyl, pyrimidinyl, pyrazinyl, benzothienyl, benzothiazolyl, benzotriazolyl, thienopyrrolyl, thienothienyl, imidazothiazolyl, or dibenzofuranyl.

3. The method of claim 1, wherein the compound is selected from the group consisting of:
8-benzyl-2-(3-methoxybenzyl)-6-phenylimidazo[1,2-a]pyrazin-3(7H)-one;
8-benzyl-2-(3-hydroxybenzyl)-6-phenylimidazo[1,2-a]pyrazin-3(7H)-one;
8-benzyl-2-(4-methoxybenzyl)-6-phenylimidazo[1,2-a]pyrazin-3(7H)-one;
tert-butyl (3-((8-benzyl-3-oxo-6-phenyl-3,7-dihydroimidazo[1,2-a]pyrazin-2-yl)methyl)phenyl)carbamate;
8-benzyl-2-((5-methoxythiophen-2-yl)methyl)-6-phenylimidazo[1,2-a]pyrazin-3(7H)-one;
2-(3-aminobenzyl)-8-benzyl-6-phenylimidazo[1,2-a]pyrazin-3(7H)-one;
8-benzyl-2-(4-(tert-butyl)benzyl)-6-phenylimidazo[1,2-a]pyrazin-3(7H)-one;
8-benzyl-2-(naphthalen-2-ylmethyl)-6-phenylimidazo[1,2-a]pyrazin-3(7H)-one;
2-([1,1'-biphenyl]-4-ylmethyl)-8-benzyl-6-phenylimidazo[1,2-a]pyrazin-3(7H)-one;
2-((2H-chromen-3-yl)methyl)-8-benzyl-6-phenylimidazo[1,2-a]pyrazin-3(7H)-one;
8-benzyl-2-((1,3-diphenyl-1H-pyrazol-4-yl)methyl)-6-phenylimidazo[1,2-a]pyrazin-3(7H)-one;
8-benzyl-2-(dibenzo[b,d]furan-4-ylmethyl)-6-phenylimidazo[1,2-a]pyrazin-3(7H)-one;
tert-butyl (4-((8-benzyl-3-oxo-6-phenyl-3,7-dihydroimidazo[1,2-a]pyrazin-2-yl)methyl)phenyl)carbamate;
2-(4-aminobenzyl)-8-benzyl-6-phenylimidazo[1,2-a]pyrazin-3(7H)-one;
2-(4-(allyloxy)-3-methoxybenzyl)-8-benzyl-6-phenylimidazo[1,2-a]pyrazin-3(7H)-one;
8-benzyl-2-(4-hydroxy-3-methoxybenzyl)-6-phenylimidazo[1,2-a]pyrazin-3(7H)-one;
8-benzyl-2-((5-((4-methyl-4H-1,2,4-triazol-3-yl)thio)furan-2-yl)methyl)-6-phenylimidazo[1,2-a]pyrazin-3(7H)-one;
8-benzyl-6-phenyl-2-((5-(pyridin-2-yl)thiophen-2-yl)methyl)imidazo[1,2-a]pyrazin-3(7H)-one 2-(benzo[b]thiophen-3-ylmethyl)-8-benzyl-6-phenylimidazo[1,2-a]pyrazin-3(7H)-one;
2-(benzo[b]thiophen-2-ylmethyl)-8-benzyl-6-phenylimidazo[1,2-a]pyrazin-3(7H)-one;
8-benzyl-6-phenyl-2-(pyridin-4-ylmethyl)imidazo[1,2-a]pyrazin-3(7H)-one;
8-benzyl-2-((5-cyclohexylthiophen-2-yl)methyl)-6-phenylimidazo[1,2-a]pyrazin-3(7H)-one;
2-([2,2'-bithiophen]-5-ylmethyl)-8-benzyl-6-phenylimidazo[1,2-a]pyrazin-3(7H)-one;
8-benzyl-2-((5-isobutylthiophen-2-yl)methyl)-6-phenylimidazo[1,2-a]pyrazin-3(7H)-one;
8-benzyl-2-((5-(1-methyl-5-(trifluoromethyl)-1H-pyrazol-3-yl)thiophen-2-yl)methyl)-6-phenylimidazo[1,2-a]pyrazin-3(7H)-one;
8-benzyl-6-phenyl-2-((5-(trifluoromethyl)furan-2-yl)methyl)imidazo[1,2-a]pyrazin-3(7H)-one;
4-((8-benzyl-3-oxo-6-phenyl-3,7-dihydroimidazo[1,2-a]pyrazin-2-yl)methyl)benzoic acid;
8-benzyl-2-((5-(methoxymethyl)furan-2-yl)methyl)-6-phenylimidazo[1,2-a]pyrazin-3(7H)-one;
8-benzyl-2-((1-methyl-3-(thiophen-2-yl)-1H-pyrazol-5-yl)methyl)-6-phenylimidazo[1,2-a]pyrazin-3(7H)-one;
8-benzyl-2-(3,5-bis(trifluoromethyl)benzyl)-6-phenylimidazo[1,2-a]pyrazin-3(7H)-one;
8-benzyl-2-((5-methylfuran-2-yl)methyl)-6-phenylimidazo[1,2-a]pyrazin-3(7H)-one;
3-((8-benzyl-3-oxo-6-phenyl-3,7-dihydroimidazo[1,2-a]pyrazin-2-yl)methyl)benzoic acid;
8-benzyl-2-((5-(morpholinomethyl)furan-2-yl)methyl)-6-phenylimidazo[1,2-a]pyrazin-3(7H)-one;
2-(3-(aminomethyl)benzyl)-8-benzyl-6-phenylimidazo[1,2-a]pyrazin-3(7H)-one;
5-((8-benzyl-3-oxo-6-phenyl-3,7-dihydroimidazo[1,2-a]pyrazin-2-yl)methyl)-1,3-dimethylpyrimidine-2,4(1H,3H)-dione;
8-benzyl-2-(imidazo[2,1-b]thiazol-6-ylmethyl)-6-phenylimidazo[1,2-a]pyrazin-3(7H)-one;
N-(3-((8-benzyl-3-oxo-6-phenyl-3,7-dihydroimidazo[1,2-a]pyrazin-2-yl)methyl)phenyl)methanesulfonamide;
8-benzyl-2-((3,5-dimethylisoxazol-4-yl)methyl)-6-phenylimidazo[1,2-a]pyrazin-3(7H)-one;
8-benzyl-6-phenyl-2-(pyridin-3-ylmethyl)imidazo[1,2-a]pyrazin-3(7H)-one;
8-benzyl-2-(4-methoxy-3-(methoxymethyl)benzyl)-6-phenylimidazo[1,2-a]pyrazin-3(7H)-one;
8-benzyl-2-(3-(dimethylamino)benzyl)-6-phenylimidazo[1,2-a]pyrazin-3(7H)-one;
8-benzyl-2-((5-(methoxymethyl)thiophen-2-yl)methyl)-6-phenylimidazo[1,2-a]pyrazin-3(7H)-one;
8-benzyl-2-(3-(methoxymethyl)benzyl)-6-phenylimidazo[1,2-a]pyrazin-3(7H)-one;
8-benzyl-2-(3-(hydroxymethyl)benzyl)-6-phenylimidazo[1,2-a]pyrazin-3(7H)-one;
8-benzyl-2-((2-methoxypyrimidin-5-yl)methyl)-6-phenylimidazo[1,2-a]pyrazin-3(7H)-one;
8-benzyl-2-((3,4-dimethylthieno[2,3-b]thiophen-2-yl)methyl)-6-phenylimidazo[1,2-a]pyrazin-3(7H)-one;
8-benzyl-6-phenyl-2-(pyrazin-2-ylmethyl)imidazo[1,2-a]pyrazin-3(7H)-one;
8-benzyl-6-phenyl-2-((2-(propylthio)pyrimidin-5-yl)methyl)imidazo[1,2-a]pyrazin-3(7H)-one;
8-benzyl-2-((4-methyl-4H-thieno[3,2-b]pyrrol-5-yl)methyl)-6-phenylimidazo[1,2-a]pyrazin-3(7H)-one;
2-((1,2,3-thiadiazol-5-yl)methyl)-8-benzyl-6-phenylimidazo[1,2-a]pyrazin-3(7H)-one;
8-benzyl-2-((1-methyl-1H-benzo[d][1,2,3]triazol-5-yl)methyl)-6-phenylimidazo[1,2-a]pyrazin-3(7H)-one;
8-benzyl-2-(3,4-dimethoxybenzyl)-6-phenylimidazo[1,2-a]pyrazin-3(7H)-one;
8-benzyl-2-(3-(methylthio)benzyl)-6-phenylimidazo[1,2-a]pyrazin-3(7H)-one;
2-(benzo[d][1,3]dioxol-5-ylmethyl)-8-benzyl-6-phenylimidazo[1,2-a]pyrazin-3(7H)-one;
8-benzyl-2-(3-((dimethylamino)methyl)benzyl)-6-phenylimidazo[1,2-a]pyrazin-3(7H)-one;
8-benzyl-2-(3-ethoxybenzyl)-6-phenylimidazo[1,2-a]pyrazin-3(7H)-one;
8-benzyl-2-((6-methylpyridin-3-yl)methyl)-6-phenylimidazo[1,2-a]pyrazin-3(7H)-one;
8-benzyl-2-((6-(dimethylamino)pyridin-3-yl)methyl)-6-phenylimidazo[1,2-a]pyrazin-3(7H)-one;
8-benzyl-2-((5-methoxypyridin-3-yl)methyl)-6-phenylimidazo[1,2-a]pyrazin-3(7H)-one;
8-benzyl-2-((6-methoxypyridin-3-yl)methyl)-6-phenylimidazo[1,2-a]pyrazin-3(7H)-one;
8-benzyl-2-((2,6-dimethoxypyridin-3-yl)methyl)-6-phenylimidazo[1,2-a]pyrazin-3(7H)-one;
8-benzyl-2-(3-(2-methoxyethoxy)benzyl)-6-phenylimidazo[1,2-a]pyrazin-3(7H)-one; and
3-((8-benzyl-3-oxo-6-phenyl-3,7-dihydroimidazo[1,2-a]pyrazin-2-yl)methyl)benzonitrile;
or a pharmaceutically acceptable salt thereof.

4. The method of claim 1, wherein the sample contains live cells.

5. The method of claim 1, wherein the sample contains a coelenterazine-utilizing luciferase.

6. A method for detecting luminescence in a transgenic animal expressing a coelenterazine-utilizing luciferase, the method comprising:
(a) administering to the transgenic animal that expresses the coelenterazine-utilizing luciferase a compound of formula (I):

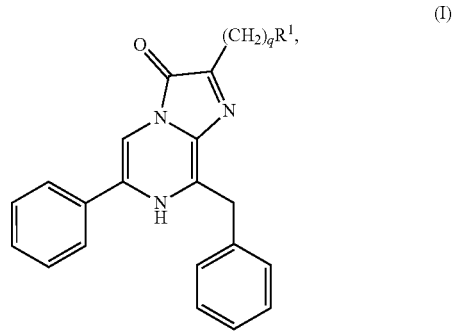

or a pharmaceutically acceptable salt or tautomer thereof,
wherein:
$R^1$ is heterocyclyl, aryl, or heteroaryl, wherein the heterocyclyl, aryl, or heteroaryl is optionally substituted with 1, 2, 3, 4, 5, 6, or 7 substituents independently selected from the group consisting of oxo, thioxo, nitro, cyano, hydroxy, alkyl, haloalkyl, hydroxyalkyl, alkoxyalkyl, aminoalkyl, alkoxyfluoroalkyl, cycloalkylalkyl, heterocyclylalkyl, arylalkyl, heteroarylalkyl, alkenyl, alkynyl, alkoxy, haloalkoxy, allyloxy, benzyloxy, aryloxy, silyloxy, sulfanyl, alkylsulfanyl, amino, alkylamino, acylamino, arylamino, sulfinylamino, sulfonylamino, acyl, carboxy, carbamate, amido, sulfinyl, sulfonyl, silyl, cycloalkyl, cycloalkenyl, heterocyclyl, aryl, and heteroaryl; and q is 1;

with the proviso that:

$R^1$ is not selected from the group consisting of:

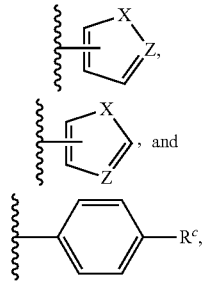

wherein:

$R^c$ is H, OH, OC(O)$C_1$-$C_7$ alkyl, or OCH$_2$OC(O) $C_1$-$C_7$ alkyl;

X is NH, N(CH$_3$), N(CH$_2$CH$_3$), S, or O; and

Z is CH or N; and (b) detecting luminescence.

7. The method of claim 6, wherein
$R^1$ is chromenyl, benzodioxolyl, 1,3-dimethylpyrimidine-2,4(1H,3H)-dionyl, phenyl, naphthalenyl, pyrazolyl, furanyl, thienyl, thiazolyl, thiadiazolyl, isoxazolyl pyridinyl, pyrimidinyl, pyrazinyl, benzothienyl, benzothiazolyl, benzotriazolyl, thienopyrrolyl, thienothienyl, imidazothiazolyl, or dibenzofuranyl.

8. The method of claim 6, wherein the compound is selected from the group consisting of:
8-benzyl-2-(3-methoxybenzyl)-6-phenylimidazo[1,2-a]pyrazin-3(7H)-one;
8-benzyl-2-(3-hydroxybenzyl)-6-phenylimidazo[1,2-a]pyrazin-3(7H)-one;
8-benzyl-2-(4-methoxybenzyl)-6-phenylimidazo[1,2-a]pyrazin-3(7H)-one;
tert-butyl (3-((8-benzyl-3-oxo-6-phenyl-3,7-dihydroimidazo[1,2-a]pyrazin-2-yl)methyl)phenyl)carbamate;
8-benzyl-2-((5-methoxythiophen-2-yl)methyl)-6-phenylimidazo[1,2-a] pyrazin-3(7H)-one;
2-(3-aminobenzyl)-8-benzyl-6-phenylimidazo[1,2-a]pyrazin-3(7H)-one;
8-benzyl-2-(4-(tert-butyl)benzyl)-6-phenylimidazo[1,2-a]pyrazin-3(7H)-one;
8-benzyl-2-(naphthalen-2-ylmethyl)-6-phenylimidazo[1,2-a]pyrazin-3(7H)-one
2-([1,1'-biphenyl]-4-ylmethyl)-8-benzyl-6-phenylimidazo[1,2-a]pyrazin-3(7H)-one;
2-((2H-chromen-3-yl)methyl)-8-benzyl-6-phenylimidazo[1,2-a]pyrazin-3(7H)-one;
8-benzyl-2-((1,3-diphenyl-1H-pyrazol-4-yl)methyl)-6-phenylimidazo[1,2-a]pyrazin-3(7H)-one;
8-benzyl-2-(dibenzo[b,d]furan-4-ylmethyl)-6-phenylimidazo[1,2-a]pyrazin-3(7H)-one;
tert-butyl (4-((8-benzyl-3-oxo-6-phenyl-3,7-dihydroimidazo[1,2-a]pyrazin-2-yl)methyl)phenyl)carbamate;
2-(4-aminobenzyl)-8-benzyl-6-phenylimidazo[1,2-a]pyrazin-3(7H)-one;
2-(4-(allyloxy)-3-methoxybenzyl)-8-benzyl-6-phenylimidazo[1,2-a]pyrazin-3(7H)-one;
8-benzyl-2-(4-hydroxy-3-methoxybenzyl)-6-phenylimidazo[1,2-a]pyrazin-3(7H)-one;
8-benzyl-2-((5-((4-methyl-4H-1,2,4-triazol-3-yl)thio)furan-2-yl)methyl)-6-phenylimidazo[1,2-a]pyrazin-3 (7H)-one;
8-benzyl-6-phenyl-2-((5-(pyridin-2-yl)thiophen-2-yl)methyl)imidazo[1,2-a]pyrazin-3(7H)-one
2-(benzo[b]thiophen-3-ylmethyl)-8-benzyl-6-phenylimidazo[1,2-a]pyrazin-3(7H)-one;
2-(benzo[b]thiophen-2-ylmethyl)-8-benzyl-6-phenylimidazo[1,2-a]pyrazin-3(7H)-one;
8-benzyl-6-phenyl-2-(pyridin-4-ylmethyl)imidazo[1,2-a]pyrazin-3(7H)-one;
8-benzyl-2-((5-cyclohexylthiophen-2-yl)methyl)-6-phenylimidazo[1,2-a]pyrazin-3(7H)-one;
2-([2,2'-bithiophen]-5-ylmethyl)-8-benzyl-6-phenylimidazo[1,2-a]pyrazin-3(7H)-one;
8-benzyl-2-((5-isobutylthiophen-2-yl)methyl)-6-phenylimidazo[1,2-a]pyrazin-3(7H)-one;
8-benzyl-2-((5-(1-methyl-5-(trifluoromethyl)-1H-pyrazol-3-yl)thiophen-2-yl)methyl)-6-phenylimidazo[1,2-a]pyrazin-3(7H)-one;
8-benzyl-6-phenyl-2-((5-(trifluoromethyl)furan-2-yl)methyl)imidazo[1,2-a]pyrazin-3(7H)-one;
4-((8-benzyl-3-oxo-6-phenyl-3,7-dihydroimidazo[1,2-a]pyrazin-2-yl)methyl)benzoic acid;
8-benzyl-2-((5-(methoxymethyl)furan-2-yl)methyl)-6-phenylimidazo[1,2-a]pyrazin-3(7H)-one;
8-benzyl-2-((1-methyl-3-(thiophen-2-yl)-1H-pyrazol-5-yl)methyl)-6-phenylimidazo[1,2-a]pyrazin-3(7H)-one;
8-benzyl-2-(3,5-bis(trifluoromethyl)benzyl)-6-phenylimidazo[1,2-a]pyrazin-3(7H)-one;
8-benzyl-2-((5-methylfuran-2-yl)methyl)-6-phenylimidazo[1,2-a]pyrazin-3(7H)-one;
3-((8-benzyl-3-oxo-6-phenyl-3,7-dihydroimidazo[1,2-a]pyrazin-2-yl)methyl)benzoic acid;
8-benzyl-2-((5-(morpholinomethyl)furan-2-yl)methyl)-6-phenylimidazo[1,2-a]pyrazin-3(7H)-one;
2-(3-(aminomethyl)benzyl)-8-benzyl-6-phenylimidazo[1,2-a]pyrazin-3(7H)-one;
5-((8-benzyl-3-oxo-6-phenyl-3,7-dihydroimidazo[1,2-a]pyrazin-2-yl)methyl)-1,3-dimethylpyrimidine-2,4(1H,3H)-dione;
8-benzyl-2-(imidazo[2,1-b]thiazol-6-ylmethyl)-6-phenylimidazo[1,2-a]pyrazin-3(7H)-one;
N-(3-((8-benzyl-3-oxo-6-phenyl-3,7-dihydroimidazo[1,2-a]pyrazin-2-yl)methyl)phenyl)methanesulfonamide;
8-benzyl-2-((3,5-dimethylisoxazol-4-yl)methyl)-6-phenylimidazo[1,2-a]pyrazin-3(7H)-one;
8-benzyl-6-phenyl-2-(pyridin-3-ylmethyl)imidazo[1,2-a]pyrazin-3(7H)-one;
8-benzyl-2-(4-methoxy-3-(methoxymethyl)benzyl)-6-phenylimidazo[1,2-a]pyrazin-3(7H)-one;
8-benzyl-2-(3-(dimethylamino)benzyl)-6-phenylimidazo[1,2-a]pyrazin-3(7H)-one;
8-benzyl-2-((5-(methoxymethyl)thiophen-2-yl)methyl)-6-phenylimidazo[1,2-a]pyrazin-3(7H)-one;
8-benzyl-2-(3-(methoxymethyl)benzyl)-6-phenylimidazo[1,2-a]pyrazin-3(7H)-one;
8-benzyl-2-(3-(hydroxymethyl)benzyl)-6-phenylimidazo[1,2-a]pyrazin-3(7H)-one;
8-benzyl-2-((2-methoxypyrimidin-5-yl)methyl)-6-phenylimidazo[1,2-a]pyrazin-3(7H)-one;
8-benzyl-2-((3,4-dimethylthieno[2,3-b]thiophen-2-yl)methyl)-6-phenylimidazo[1,2-a]pyrazin-3(7H)-one;
8-benzyl-6-phenyl-2-(pyrazin-2-ylmethyl)imidazo[1,2-a]pyrazin-3(7H)-one;

8-benzyl-6-phenyl-2-((2-(propylthio)pyrimidin-5-yl)methyl)imidazo[1,2-a]pyrazin-3(7H)-one;
8-benzyl-2-((4-methyl-4H-thieno[3,2-b]pyrrol-5-yl)methyl)-6-phenylimidazo[1,2-a]pyrazin-3(7H)-one;
2-((1,2,3-thiadiazol-5-yl)methyl)-8-benzyl-6-phenylimidazo[1,2-a]pyrazin-3(7H)-one;
8-benzyl-2-((1-methyl-1H-benzo[d][1,2,3]triazol-5-yl)methyl)-6-phenylimidazo[1,2-a]pyrazin-3(7H)-one;
8-benzyl-2-(3,4-dimethoxybenzyl)-6-phenylimidazo[1,2-a]pyrazin-3(7H)-one;
8-benzyl-2-(3-(methylthio)benzyl)-6-phenylimidazo[1,2-a]pyrazin-3(7H)-one;
2-(benzo[d][1,3]dioxol-5-ylmethyl)-8-benzyl-6-phenylimidazo[1,2-a]pyrazin-3(7H)-one;
8-benzyl-2-(3-((dimethylamino)methyl)benzyl)-6-phenylimidazo[1,2-a]pyrazin-3(7H)-one;
8-benzyl-2-(3-ethoxybenzyl)-6-phenylimidazo[1,2-a]pyrazin-3(7H)-one;
8-benzyl-2-((6-methylpyridin-3-yl)methyl)-6-phenylimidazo[1,2-a]pyrazin-3(7H)-one;
8-benzyl-2-((6-(dimethylamino)pyridin-3-yl)methyl)-6-phenylimidazo[1,2-a]pyrazin-3(7H)-one;
8-benzyl-2-((5-methoxypyridin-3-yl)methyl)-6-phenylimidazo[1,2-a]pyrazin-3(7H)-one;
8-benzyl-2-((6-methoxypyridin-3-yl)methyl)-6-phenylimidazo[1,2-a]pyrazin-3(7H)-one;
8-benzyl-2-((2,6-dimethoxypyridin-3-yl)methyl)-6-phenylimidazo[1,2-a]pyrazin-3(7H)-one;
8-benzyl-2-(3-(2-methoxyethoxy)benzyl)-6-phenylimidazo[1,2-a]pyrazin-3(7H)-one; and
3-((8-benzyl-3-oxo-6-phenyl-3,7-dihydroimidazo[1,2-a]pyrazin-2-yl)methyl)benzonitrile;
or a pharmaceutically acceptable salt thereof.

\* \* \* \* \*